(12) United States Patent
Malick et al.

(10) Patent No.: US 9,207,240 B2
(45) Date of Patent: *Dec. 8, 2015

(54) METHOD OF EFFICIENT EXTRACTION OF PROTEIN FROM CELLS

(75) Inventors: Adrien P. Malick, Granite, MD (US); Virginia M. Crews, Baltimore, MD (US); Julie L. Rosales, Randallstown, MD (US); Carrie S. Ferguson, Bel Air, MD (US); Jeff H. Bruton, Randallstown, MD (US); Robert J. Beadenkopf, Pasadena, MD (US); John Mantlo, Westminster, MD (US)

(73) Assignee: ARBOR VITA CORPORATION, Fremont, CA (US)

( * ) Notice: Subject to any disclaimer, the term of this patent is extended or adjusted under 35 U.S.C. 154(b) by 794 days.

This patent is subject to a terminal disclaimer.

(21) Appl. No.: 11/985,547

(22) Filed: Nov. 14, 2007

(65) Prior Publication Data

US 2009/0123910 A1 May 14, 2009

(51) Int. Cl.
C12N 15/52 (2006.01)
C07K 1/14 (2006.01)
G01N 33/569 (2006.01)

(52) U.S. Cl.
CPC .......... *G01N 33/56983* (2013.01); *C07K 1/145* (2013.01); *C12N 15/52* (2013.01); *C12N 2710/20022* (2013.01); *G01N 2333/16* (2013.01); *G01N 2469/10* (2013.01)

(58) Field of Classification Search
None
See application file for complete search history.

(56) References Cited

U.S. PATENT DOCUMENTS

| | | | |
|---|---|---|---|
| 3,303,038 A | 2/1967 | Klevens | |
| 3,546,334 A | 12/1970 | Lerner et al. | |
| 3,862,112 A | 1/1975 | Ishida et al. | |
| 4,578,282 A | 3/1986 | Harrison | |
| 4,649,192 A * | 3/1987 | Van Wijnendaele et al. | 530/371 |
| 4,857,300 A | 8/1989 | Maksem | |
| 5,104,640 A | 4/1992 | Stokes | |
| 5,132,205 A | 7/1992 | Pronovost et al. | |
| 5,196,182 A | 3/1993 | Ryan | |
| 5,256,571 A | 10/1993 | Hurley et al. | |
| 5,432,056 A | 7/1995 | Hartman et al. | |
| 5,620,869 A | 4/1997 | Woodard et al. | |
| 5,773,277 A * | 6/1998 | Hashimoto et al. | 435/232 |
| 6,004,771 A | 12/1999 | Thornton | |
| 6,245,568 B1 | 6/2001 | Volkin et al. | |
| 6,337,189 B1 | 1/2002 | Ryan | |
| 6,488,671 B1 | 12/2002 | Constantz et al. | |
| 6,890,729 B2 | 5/2005 | Mielzynska et al. | |
| 7,115,719 B2 | 10/2006 | Paulsen | |
| 7,306,926 B2 * | 12/2007 | Doeberitz et al. | 435/7.23 |
| 8,962,262 B2 | 2/2015 | Lovell et al. | |
| 2003/0175852 A1 * | 9/2003 | Kalra et al. | 435/40.5 |
| 2004/0018487 A1 | 1/2004 | Lu et al. | |
| 2004/0101947 A1 | 5/2004 | Engel et al. | |
| 2004/0180388 A1 | 9/2004 | Von Knebel et al. | |
| 2005/0019841 A1 | 1/2005 | Garman et al. | |
| 2005/0032105 A1 | 2/2005 | Bair et al. | |
| 2005/0037969 A1 | 2/2005 | Lu et al. | |
| 2005/0112552 A1 | 5/2005 | Herrero et al. | |
| 2005/0142541 A1 | 6/2005 | Lu et al. | |
| 2006/0148711 A1 | 7/2006 | Lu et al. | |
| 2007/0292899 A1 * | 12/2007 | Lovell et al. | 435/7.21 |
| 2015/0266928 A1 | 9/2015 | Lovell et al. | |

FOREIGN PATENT DOCUMENTS

| | | |
|---|---|---|
| EP | 0174106 A2 | 3/1986 |
| EP | 0174106 A3 | 3/1986 |
| EP | 0 363 108 A2 | 4/1990 |
| EP | 0 363 110 A2 | 4/1990 |
| EP | 0382519 A2 | 8/1990 |
| EP | 0 363 108 A3 | 7/1991 |
| EP | 0 363 110 A3 | 7/1991 |
| EP | 0363110 B1 | 9/1995 |
| JP | H03-43094 A | 2/1991 |
| JP | 2004534831 A | 11/2004 |
| JP | 2005-538360 | 12/2005 |
| WO | WO 00/57906 A1 | 10/2000 |
| WO | WO-03000877 A2 | 1/2003 |
| WO | WO 2005/088311 A1 | 9/2005 |
| WO | WO 2007/134252 A1 | 11/2007 |

OTHER PUBLICATIONS

Veerisetty et al. (Phytopathology, 1977, vol. 68, p. 59-64).*
Demay, Common Problem in Papanicolaou Smear Interpretation. Arch. Pathol. Lab. Med. 1997; 121:229-238.
Harlow, et al. Antibodies: A Laboratory Manual Cold Spring Harbor Laboratory Cold Spring Harbor. N.Y. 1988.
Hatefi, et al. Solubilization of particulate proteins and agents. Proc. Natl. Acad. Sci. 1969; 62;1129-1136.
Koss. The Papanicolaon Test for Cervical Cancer Detection: A Triumph and a Tragedy. JAMA. 1989; 261; 737-743.
O'Neil et al. Eds. Polyoxyethyene Alcohols, No. 7659 The Merck Index. 13th Edition. Merck Research Laboratories. 2001, 7663.
Priciples and standard conditions for purification techniques. Protein purification Handbook, Amersham Pharmacia Biotech. 1999; 71-95.
Schneider, et al. Mutagenesis and selection of PDZ domains that bind new protein targets. Nat. Biotech. 1999;17:170-175.
Umbreit, et al. Relation of detergent HLB number to solubilization and stabilization of D-alanine carboxypeptidase from *Bacillus subtillis* membreanes. Proc. Natl. Acad. Sci. USA. 1973; 70: 2997.

(Continued)

*Primary Examiner* — Benjamin P. Blumel

(74) *Attorney, Agent, or Firm* — Wilson Sonsini Goodrich Rosati

(57) ABSTRACT

Methods for producing a protein extract from cells, such as cells or cellular samples containing viral proteins, are provided. In general terms, the methods may involve: increasing the pH of the cells to a pH of at least about pH 10.0 to produce an intermediate composition, and then, in the presence of a non-ionic detergent such as a polyoxyethylene alkyl ether, neutralizing the pH of the intermediate composition to produce the protein extract. Such methods can be used in conjunction with methods for detecting one or more target proteins in a sample, such as viral proteins. Systems, kits and compositions for practicing the subject methods are also provided.

45 Claims, 8 Drawing Sheets

(56) References Cited

OTHER PUBLICATIONS

Williams, et al. Tissue Preparation for Immunocytochemisty. J Clin. Pathol. 1997;50;422-428

Romeo, et al. Infrared micro-spectroscopic studies of epithelial cells. Biochim Biophys Acta. 2006; 1758(7):915-22.

Gu, et al. Proteomic analysis of high-grade dysplastic cervical cells obtained from ThinPrep slides using laser capture microdissection and mass spectrometry. J Proteome Res. 2007; 6(11):4256-68.

Bosch, et al. The Aetiology of Cervical Cancer. NHS Cancer Screening Programmes. 2005.

Elshal, et al. Multiplex bead array assays: performance evaluation and comparison of sensitivity to ELISA. Methods. 2006; 38(4):317-23.

Vignali. Multiplexed particle-based flow cytometric assays. J Immunol Methods. 2000; 243(1-2):243-55.

Elston, et al. The identification of a conserved binding motif within human papillomavirus type 16 E6 binding peptides, E6AP and E6BP. J Gen Virol. Feb. 1998;79 ( Pt 2):371-4.

European search report and searh opinion dated Dec. 2, 2010 for Application No. 07797439.2.

European search report dated Dec. 3, 2010 for Application No. 08850323.

International search report dated Jan. 27, 2009 for PCT Application No. US2008/83707.

Office action dated Feb. 1, 2011 for U.S. Appl. No. 11/747,830.
Office action dated Jun. 10, 2010 for U.S. Appl. No. 11/747,830.
Office action dated Sep. 30, 2009 for U.S. Appl. No. 11/747,830.
Office action dated Oct. 13, 2011 for U.S. Appl. No. 11/747,830.
European office action dated Mar. 29, 2012 for EP Application No. 07797439.2.
European office action dated Mar. 29, 2012 for EP Application No. 08850323.0.
European office action dated Sep. 6, 2012 for EP Application No. 08850323.0.
European office action dated Sep. 10, 2012 for EP Application No. 07797439.2.
European office action dated Sep. 10, 2012 for EP Application No. 08850323.0.
International search report dated Oct. 29, 2007 for PCT Application No. US2007/68809.
Office action dated Oct. 11, 2012 for U.S. Appl. No. 11/747,830.
Notice of allowance dated Oct. 24, 2014 for U.S. Appl. No. 11/747,830.
Office action dated Mar. 21, 2014 for U.S. Appl. No. 11/747,830.
Office action dated Aug. 23, 2013 for U.S. Appl. No. 11/747,830.
Yan, Qunfang. The Characteristic and Application of Nonionic Surfactant (in Chinese with English abstract) Guizhou Chemical Industry. Oct. 2005; 30(5):4-7 and 22.
U.S. Appl. No. 14/598,148, filed Jan. 15, 2015, Lovell et al.
Ausubel, et al. Current Protocols in Molecular Biology, vol. 1, Wiley & Sons, 1995.
Baker. Principles of Biological Microtechnique: A Study of Fixation and Dyeing, 1959.
Bird, et al. Single-chain antigen-binding proteins. Science. Oct. 21, 1988;242(4877):423-6.
Hood, et al. Immunology, 2nd edition, 1984.
Hunkapiller, et al. The growing immunoglobulin gene superfamily. Nature. Sep. 4-10, 1986;323(6083):15-6.
Huston, et al. Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Lanzavecchia, et al. The use of hybrid hybridomas to target human cytotoxic T lymphocytes. Eur J Immunol Jan. 1987;17(1):105-11.
Notice of allowance dated Jan. 29, 2015 for U.S. Appl. No. 11/747,830.
Notice of allowance dated Dec. 8, 2014 for U.S. Appl. No. 11/747,830.
Protein purification handbook. Amersham Pharmacia Biotech, p. 71, 1999.

\* cited by examiner

METHOD OF EFFICIENT EXTRACTION OF PROTEIN FROM CELLS

JOINT RESEARCH AGREEMENT

The invention described herein was made under a joint research agreement between Arbor Vita Corporation and Becton, Dickinson and Company.

BACKGROUND OF THE INVENTION

In many diagnostic methods, cells are taken from a subject and deposited into a liquid medium containing a fixative. The cells are fixed in the medium and examined cytologically in order to provide a diagnosis. For example, detection of precancerous or cancerous cells in cervical tissue is routinely performed by microscopic assessment of exfoliated cervical cells. This method, developed by George N. Papanicolaou and known as the "Pap" test, involves exfoliating cells from a woman's cervix using a sampling device, depositing the exfoliated cells into a transport medium that contains a fixative, and then depositing the cells onto a slide. The cells are then stained and examined by light microscopy for cellular abnormalities by a trained medical professional. Over 55 million Pap tests are performed each year in the United States alone.

Despite the success of such cytological tests, the tests are prone to error. For example, it has been estimated that up to 40% of conventional Pap tests are compromised by the presence of contaminants such as mucous, blood cells and obscuring inflammatory cells. These contaminants lead to false negative results, false positive results, and a significant amount of follow-up work. See, e.g., Koss, L. G. (1989), The Papanicolaou Test for Cervical Cancer Detection: A Triumph and a Tragedy, JAMA 261:737-743; see also DeMay, "Problems in Pap Smear Interpretation", Arch. Pathol. Lab. Med. 121:229-23 (1997).

In view of the above, there is a need for complementary molecular diagnostic methods for the analysis of cells that are present in a liquid medium containing a fixative. Such methods are not straightforward, however, because it is not always possible to perform such methods on fixed cells. For example, certain fixatives (e.g., those transport media employed in THINPREP™ or SUREPATH™ test systems) may cause particular cellular proteins to precipitate or aggregate, thereby making those proteins insoluble and difficult or impossible to reliably detect using conventional means, e.g., using an enzyme-linked immunosorbancy assay (ELISA) or another immunological test.

There is therefore a great need for methods and compositions for extracting proteins from fixed and unfixed cells in a manner that allows them to be suitable for use in molecular, e.g., immunological, detection assays. The invention described herein meets this need, and others.

SUMMARY OF THE INVENTION

Methods for producing a protein extract from cells are provided. In general terms, the methods involve: contacting a cell sample with a high pH (of at least about pH 10) extraction reagent comprising a polyoxyethylene alkyl ether (e.g. Brij™35) to produce an intermediate composition, and then, in the presence of a neutralizing reagent, neutralizing the pH of the intermediate composition, for example, to a pH value of about 6-9, optionally to a pH value of 7-8.5, to produce the protein extract. In certain embodiments, one or both of the extraction reagent and the neutralization reagent contains a polyoxyethylene alkyl ether. The cells may be fixed or unfixed exfoliated cervical cells. In certain embodiments, the methods involve extracting a target viral protein such as an HPV E6 protein from a cell sample. The invention also provides for methods for detecting the presence of a protein, such as a target viral protein, comprising producing a protein extract from fixed or unfixed cells according to the method described above and testing for the presence of said protein in said protein extract. In addition, the invention provides a system for producing a protein extract comprising: a) a cellular sample comprising fixed or unfixed cells; b) an extraction reagent that has a pH of at least about pH 10.0, and c) a neutralizing reagent wherein one or both of said extraction reagent and said neutralizing reagent comprises a polyoxyethylene alkyl ether and where said extraction reagent and neutralizing agent may be employed in the method described above to produce a protein extract suitable for use in a binding assay. Further, the invention provides a kit for producing a protein extract from fixed or unfixed cells. The kit may further comprise components and/or reagents for detecting the target protein in the protein extract.

DEFINITIONS

Figure 1A:
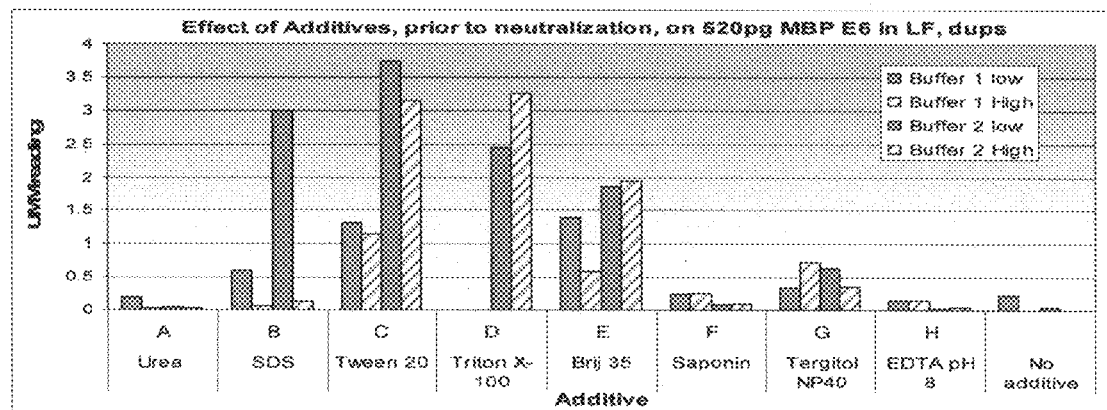
FIG. 1A demonstrates the synergistic effect on the detection of extracted HPV16 E6 protein of using an extraction reagent with a high pH combined with certain additives. Previously-purified recombinant HPV 16 E6 protein (MBP-E6) was suspended in extraction reagent and then neutralized by neutralization reagent following the protocol described herein. E6 protein was captured using a lateral flow (LF) assay described herein and detected with a UMM reader.

Unless defined otherwise, all technical and scientific terms used herein have the same meaning as commonly understood by one of ordinary skill in the art to which this invention belongs. Still, certain elements are defined below for the sake of clarity and ease of reference.

The terms "cellular sample" or "cell sample" as used herein relates to a liquid composition containing one or more cells of interest. A cellular sample may be a clinical sample containing cells removed from (e.g., dissected or exfoliated from) an individual, including but not limited to, for example, cells from plasma, serum, spinal fluid, semen, lymph fluid, the external sections of the skin, respiratory, intestinal, and genitourinary tracts, tears, saliva, milk, blood cells, tumors, or organs. In other embodiments, the cellular sample may contain cells grown in vitro (including but not limited to cells in cell culture medium, virally infected cells, recombinant cells, etc.). In certain embodiments, the cellular sample may contain cells that are at most risk of being infected by HPV. In these embodiments, the cells may be obtained from a cervix, vulva, vagina, anus, penis, mouth or throat. In certain embodiments, the cells are from mucous membrane and may be epithelial in origin. A cellular sample may or may not contain contaminants other than exfoliated or dissected cells. For example, mucous, or bacterial, yeast or blood cells may be present in a cellular sample.

"HPV" is human Papillomavirus, including but not limited to HPV strain 4, 11, 20, 24, 28, 36, 48, 50, 16, 18, 31, 35, 30, 39, 45, 51, 52, 56, 59, 58, 33, 66, 68, 69, 26, 53, 73, and 82.

An "oncogenic HPV strain" is an HPV strain that is known to cause cervical cancer as determined by the National Cancer Institute (NCI, 2001).

An "oncogenic E6 protein" is an E6 protein encoded by an oncogenic HPV strain. Exemplary oncogenic strains are: HPV 26, HPV 53, HPV 66, HPV 73, HPV 82, HPV 16, HPV 18, HPV 31, HPV 35, HPV 30, HPV 39, HPV 45, HPV 51, HPV 52, HPV 56, HPV 59, HPV 58, HPV 33, HPV 66, BPV 68, HPV 69, and HPV 82. The amino acid sequences of oncogenic E6 proteins are deposited in NCBI's GenBank database. While not wishing to be bound to the theory, it is generally believed that HPV strain 4, 11, 20, 24, 28, 36, 48, and 50 are not oncogenic.

The terms "polypeptide" and "protein" are used interchangeably. The term "polypeptide" includes polypeptides in which the conventional backbone has been replaced with non-naturally occurring or synthetic backbones, and peptides in which one or more of the conventional amino acids have been replaced with one or more non-naturally occurring or synthetic amino acids.

The term "fusion protein" or grammatical equivalents thereof references a protein composed of a plurality of polypeptide components, that while not attached in their native state, are joined by their respective amino and carboxyl termini through a peptide linkage to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, and the like.

In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 50 amino acids. In some embodiments, peptides are between 5 and 30 amino acids in length. Polypeptides may be natural in that that they may be encoded by the genome of an organism or virus, or un-natural in that they are non-naturally occurring.

The term "capture agent" refers to an agent that binds a protein through an interaction that is sufficient to permit the agent to bind and concentrate the protein from a homogeneous mixture of different proteins. Accordingly, the term "capture agent" refers to a molecule or a multi-molecular complex which can specifically bind an analyte, e.g., specifically bind an analyte for the capture agent, with a dissociation constant ($K_D$) of less than about $10^{-6}$ M without binding to other targets. The binding interaction may be mediated by an affinity region of the capture agent. Representative capture agents include antibodies (including fragments and mimetics thereof) and PDZ domain-containing proteins, etc.

The term "specific binding" refers to the ability of a capture agent to preferentially bind to a particular protein that is present in a homogeneous mixture of different proteins. In certain embodiments, a specific binding interaction will discriminate between a particular protein and other proteins in a sample, in some embodiments more than about 10 to 100-fold or more (e.g., more than about 1000- or 10,000-fold).

The term "capture agent/protein complex" is a complex that results from the specific binding of a capture agent with a protein, i.e., a "binding partner pair". A capture agent and a protein for the capture agent specifically bind to each other under "conditions suitable for specific binding", where such conditions are those conditions (in terms of salt concentration, pH, detergent, protein concentration, temperature, etc.) which allow for binding to occur between capture agents and proteins to bind in solution. Such conditions, particularly with respect to antibodies and their antigens, are well known in the art (see, e.g., Harlow and Lane (Antibodies: A Laboratory Manual Cold Spring Harbor Laboratory, Cold Spring Harbor, N.Y. (1989)). In certain embodiments, the affinity between a capture agent and protein that are specifically bound in a capture agent/protein complex is characterized by a $K_D$ (dissociation constant) of less than $10^{-6}$ M, less than $10^{-7}$ M, less than $10^{-8}$ M, less than $10^{-9}$ M, or less than about $10^{-10}$ M.

"Binding partners" and equivalents refer to pairs of molecules that can be found in a capture agent/analyte complex, i.e., exhibit specific binding with each other.

The terms "antibody" and "immunoglobulin" are used interchangeably herein to refer to a capture agent that has at least an epitope binding domain of an antibody. These terms are well understood by those in the field, and refer to a protein containing one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, gold colloidal particles, and the like. Also encompassed by the terms are Fab', Fv, $F(ab')_2$, and or other antibody fragments that retain specific binding to antigen. Antibodies could also be used in conjunction with amplifiable detector particles.

Antibodies may exist in a variety of other forms including, for example, Fv, Fab, and $(Fab')_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986)). Monoclonal antibodies and "phage display" antibodies are well known in the art and encompassed by the term "antibodies".

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present, and/or determining whether it is present or absent.

By "remote location" is meant a location other than the location at which cells are obtained and deposited into a fixative-containing liquid. For example, a remote location could be a different room in the same building in which cells are obtained (e.g., another laboratory), a different building in the same building complex as the cells are obtained, or a different location in the same city, state or country, etc. When a cellular sample is indicated as being "received" from a remote location, the cellular sample may be obtained from the remote location or hand-delivered, mailed or couriered from the remote location, for example.

"Communicating" information refers to any means of getting that information from one location to the next, whether by physically transporting printed material or computer readable media containing the information (e.g., by mail), or by transmitting the information. If information is transmitted, a digital or analog signal representing the information (e.g., a electromagnetic signal such as a light or electrical signal) is transmitted over a suitable communication channel (for example, a private, public or wireless network). Any convenient means may be employed for transmitting the data, e.g., facsimile, modem, internet, e-mail, etc.

As used herein, the term "transport medium" is used to describe liquid suitable for collection of cells and the preservation of those cells in a manner that allows them to be suitable for liquid-based cytological studies. Transport media are commonly employed in Pap test. Cells deposited into transport medium may or may not be transported from one location to another in that medium. Transport media contain fixative. Deposition of cells into a transport medium fixes the cells to produce fixed cells. Representative transport media include SUREPATH™ or PRESERVCYT™ transport media.

A "fixed cell" is a cell that has been treated with and cytologically preserved by a chemical fixative. Fixed cells are usually suitable for staining and subsequent morphological and/or cytological analysis by light microscopy.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Methods for producing a protein extract from fixed or unfixed cells are provided. In general terms, the methods involve: contacting a cell sample with a high pH (of at least about pH 10) extraction reagent comprising a polyoxyethylene alkyl ether (e.g. Brij™35) to produce an intermediate composition, and then, in the presence of a neutralizing reagent, neutralizing the pH of the intermediate composition to produce the protein extract. One or both of the extraction reagent and the neutralization reagent contains the polyoxyethylene alkyl ether. In certain embodiments, the cells may be fixed or unfixed exfoliated cervical cells. Kits and compositions for practicing the subject methods are also provided. The subject methods find use in a variety of different applications, including diagnostic tests that detect particular proteins in the resultant protein extract.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing components that are described in the publications which might be used in connection with the presently described invention.

As summarized above, the subject invention provides methods and compositions for producing a protein extract from fixed or unfixed cells. In describing the invention in greater detail, the methods are described first followed by a description of the kits and systems for use in practicing the subject methods.

Methods of Protein Extraction

As noted above, the invention provides a method for producing a protein extract from fixed or unfixed cells. In general, the methods involve two steps: a) contacting the fixed or unfixed cells with an extraction reagent having a pH that is greater than about pH. 10.0 to produce an intermediate composition and b) contacting the intermediate composition with a neutralizing reagent. The extraction reagent and/or the neutralizing reagent comprises a polyoxyethylene alkyl ether. The resultant protein extract contains a polyoxyethylene alkyl ether and has a pH that is neutral (i.e., between about pH 7.0 and about pH 8.0). The methods generally produce a protein extract containing proteins that are readily detectable using capture agents for those proteins. As such, a protein extract produced by the instant methods is generally suitable for use in binding assays, e.g., immunological assays, for detection of those proteins.

In certain embodiments the methods include: a) contacting the cells with an extraction reagent comprising a polyoxyethylene alkyl ether and a high pH to produce an intermediate composition having a pH of at least about pH 10.0, and b) contacting the intermediate composition with a neutralization reagent to neutralize said pH of the intermediate composition and produce the protein extract. Since, as mentioned above, the polyoxyethylene alkyl ether may be present in either the extraction reagent or the neutralizing reagent (or in both the extraction reagent and the neutralizing reagent), certain embodiments of the instant methods include a) and b) contacting the intermediate composition with a neutralizing reagent comprising a polyoxyethylene alkyl ether to neutralize said pH of the intermediate composition and produce the protein extract.

In certain embodiments, the protein extract produced by the instant methods may contain more protein that is accessible to capture agents than a protein extract made using other methods, e.g., methods that do not employ: a high pH extraction step (i.e., a step that increases pH to greater than about pH 10.0 or pH 11.0), a neutralizing step (i.e., a step that adjusts the pH to from about pH 7.0 to about pH 8.0) and a polyoxyethylene alkyl ether. Neither high pH alone nor a polyoxyethylene alkyl ether alone produces such a protein extract. In particular embodiments, the high pH extraction reagent solubilizes proteins in the fixed or unfixed cells, whereas the polyoxyethylene alkyl ether prevents the solubilized proteins in the intermediate composition from re-aggregating or precipitating as the pH of the intermediate composition is neutralized.

The reagents employed in the instant methods and the protein extract produced by the instant methods are described in greater detail below, as is a description of how the reagents may be used to produce the protein extract. As will be discussed below, the optimum concentration and pH of the reagents used in the instant methods may vary depending on which reagents are used. However, the optimum concentration and pH of the reagents are readily determined, either experimentally or empirically.

The Cells from Which the Protein is Extracted by Using the Inventive Method

The methodology according to the present invention can be used to extract a target protein or protein of interest from a sample of cells. The sample of cells may be a homogenous population of cells, or a heterogenous mixture of cells of different type. The sample of cell may also contain "contaminants" such as mucous, blood cells and inflammatory cells which are not of interest for the purpose of extraction of the target protein or do not contain the target protein.

In some embodiments, the target protein is a viral protein present in cells infected with a virus, preferably a pathological virus, and the cells are preferably ones isolated from a mammal, e.g., a human.

The pathogenic virus may be any pathogenic virus that causes pathogenic effects or disease in human or other animals. The pathogenic virus may be various strains of human immunodeficiency virus (HIV), such as HIV-1 and HIV-2. The viral protein may be an HIV glycoprotein (or surface antigen) such as HIV GP120 and GP41, or a capsid protein (or structural protein) such as HIV P24 protein.

The pathogenic virus may be Ebola or Marburg virus. The viral protein may be an Ebola glycoprotein or surface antigen such as Ebola GP1 or GP2 protein.

The pathogenic virus may be hepatitis virus such as hepatitis A, B, C, D or E virus. For example, the viral protein may be a surface antigen or core protein of hepatitis B virus such as the small hepatitis B surface antigen (SHBsAg) (also referred to as the Australia antigen), the middle hepatitis B surface antigen (MHBsAg) and the large hepatitis B surface antigen (LHBsAg). The viral antigen may be a surface antigen or core protein of hepatitis C virus such as NS3, NS4 and NS5 antigens.

The pathogenic virus may be a respiratory syncytial virus (RSV). For example, the RSV viral protein may be the glycoprotein (G-protein) or the fusion protein (F-protein) of RSV.

The pathogenic virus may be a herpes simplex virus (HSV) such as HSV-1 and HSV-2. For example, the HSV viral antigen may be the glycoprotein D from HSV-2.

The target protein may be a tumor antigen, such as Her 2 of breast cancer cells and CD20 on lymphoma cells, a viral oncogene such as E6 and E7 of human papilloma virus, or a cellular oncogene such as mutated ras.

In some embodiments, the sample of cells contains fixed cells in which the target protein is present. The fixed cells employed in the instant methods are generally obtained by depositing a sample of cells (obtained by removing cells from a subject by dissection, exfoliation or lavage, for example) into a liquid medium. The sample of cells may be deposited into a liquid medium that already contains a chemical fixative, or a chemical fixative may be added to the liquid medium after the cells have been placed in the medium. A liquid medium containing a fixative and fixed cells is included, along with unfixed cells, within the meaning of the term "cellular sample" herein.

Representative chemical fixatives that may be employed in the instant methods include: alcohols (e.g., methanol or ethanol), aldehydes (e.g., gluteraldehyde or formaldehyde) and ketones (e.g., acetone), as well as osmium tetroxide, acetic acid, picric acid and heavy metal ion salts. Further examples of fixatives that may be employed in the instant methods include bi-sulfite-based fixatives (that may also include acetic acid), PVP-based fixatives (that may also contain propylene glycol and methanol) as well as those described in U.S. Pat. Nos. 3,546,334, 4,578,282, 4,857,300, 5,104,640, 5,256,571, 5,432,056 and 5,196,182. Examples of fixatives that may be employed in the instant methods, including the working concentrations of those fixatives, may be found in Baker, (Principles of Biological Microtechnique: A Study of Fixation and Dyeing, 1959) and Williams ("Tissue preparation for immunocytochemistry." J Clin. Pathol. 1997 50:422).

Of particular interest in the instant methods are liquid media that are termed "transport media" and routinely used for the collection, preservation (i.e., fixation) and transport of cervicovaginal cells (e.g., exfoliated cervical cells) as part of a gynecological examination. FDA approved transport media are of particular interest.

Examples of commercially available transport media that may be employed include: methanol-based PRESERV-CYT™ transport medium (which is sold as part of the THINPREP™ gynecological sampling kit of Cytyc, Inc., Marlborough, Mass.), ethanol-based SUREPATH™ transport medium formally known as CYTORICH™ (TriPath, Inc. Burlington, N.C.), and methanol-based CYTOLYT™ transport medium (Cytyc, Inc., Marlborough, Mass.) for example.

Cells may be obtained by any convenient method, including but not limited to exfoliation (e.g., scraping), dissection and lavage. Of particular interest are epithelial cells of cervical origin, which cells are typically obtained by exfoliating methods using an adapted brush, swab, spatula or scraper, and deposited into a liquid medium containing or not containing fixative.

Extraction Reagent

The extraction reagent employed in the instant methods contains components that are present in amounts sufficient in concentration to produce a protein extract having a pH that is at least pH 10.0, upon addition of the extraction reagent to cells. Accordingly, the extraction reagent generally has a pH of at least about pH 10.0.

The extraction reagent is contacted with the cells to produce the intermediate composition. The pH of the extraction reagent and resulting intermediate composition is generally at least about pH 10.0, e.g., in the range of about pH 10.0 to about pH 13.0 or about pH 12.0 to about pH 13.0. In certain embodiments, the extraction reagent may have a pH of about pH 10.0 to about pH 10.5, pH 10.5 to about pH 11.0, pH 11.0 to about pH 11.5, pH 11.5 to about pH 12.0, pH 12.0 to about pH 12.5 or pH 12.5 to about pH 13.0. In certain preferred embodiments, the extraction reagent has a pH of about pH 12.5 to about pH 12.9. Extraction reagent may be made using any suitable source of hydroxide ions, e.g., sodium or potassium hydroxide or calcium carbonate, for example.

In certain embodiments, the extraction reagent may contain a buffer to maintain the reagent at a desired pH. If a buffer is present in a subject extraction reagent, the buffer may have a $pK_a$ in the range of about 9.0 to about 12.5 at 25° C. Exemplary buffers that may be employed in a subject protein extraction reagent include CABS, piperidine, phosphate, CAPS, glycine or ethanolamine, for example. The extraction reagent employed in the instant methods contains components that are present in amounts sufficient in concentration to produce a protein extract having a pH that is at least pH 10.0, upon addition of the extraction reagent to fixed or unfixed cells. Accordingly, the extraction reagent generally has a pH of at least about pH 10.0.

In preferred embodiments the extraction reagent comprises TriSodium Citrate and NaOH. An exemplary extraction reagent comprises about 0.1N NaOH, about 50 mM TriSodium Citrate, and a pH of 12.5 to 12.9.

In some preferred embodiments, the amount or pH of the extraction reagent necessary to bring the sample to the target pH, e.g. pH of more than pH 10, will be pre-determined empirically prior to addition of the extraction reagent. In such embodiments, the empirically-determined extraction reagent will be added to the cellular sample. In other embodiments, following addition of the extraction reagent, the pH of the intermediate composition will be measured. After such measurement step, the pH will be adjusted, if necessary, to achieve the targeted pH.

The extraction reagent may also comprise one or more, or mixture of: HEPES, Triton™X-100, NaCl, glycerol and EGTA. An exemplary extraction reagent may comprise about 50 mM HEPES, pH about pH 7.5, about 1.1% Triton™X-100, about 150 mM NaCl, about 10% glycerol, and about 1 mM EGTA.

In certain embodiments, in addition to having a pH of at least 10.0, the extraction reagent may also contain a polyoxyethylene alkyl ether of the formula $CH_3(CH2)_{n1}CH_2(OCH_2CH_2)_{n2}OH$. Such polyoxyethylene alkyl ethers, also known as polyoxyethylene alcohols, are commonly used as emulsifiers, wetting agents, solubilizers, defoamers, detergents and/or lubricants in industrial, cosmetic, and pharmaceutical applications. (See, e.g. The Merck Index. $13^{th}$ Edition, 7659). In certain embodiments the polyoxyethylene alkyl ether is a Brij™ surfactant such as Brij™35 or other Brij™ family member described herein.

Brij™35 CAS [9002-92-0] is a non-ionic surfactant commonly used in High Performance Liquid Chromatography (HPLC) applications for the isolation of membrane complexes. It is often employed to prevent nonspecific binding to chromatogaphy supports. It has a Hydrophile-Lipophile Balance Number (HLB) of 16.9, indicating that it is a hydrophillic compound capable of being used as a solubilizing agent, such as the nondenaturing solubilization of membran proteins, or as an emulsifier. (See, e.g. Umbreit, J. N., and Strominger, J. L. 1973. Relation of detergent HLB number to solubilization and stabilization of D-alanine carboxypeptidase from *Bacillus subtillis* membreanes. Proc. Natl. Acad. Sci. USA 70, 2997).

Brij™35, contains a lauryl group ($CH_3(CH2)_{10}CH_2$) and 23 ethyleneoxy ($OCH_2CH_2$) units and has the chemical formula $CH_3(CH2)_{10}CH_2(OCH_2CH_2)_{23}OH$. Other chemical synonyms include: polyoxyethylene lauryl ether; LAU- RETH-23; polyoxyethylene (23) lauryl ether $C_{12}E_{23}$; Polyoxyethyleneglycol dodecyl ether; Lauryl Alcohol Ethylene Oxide, Ethoxylated Lauryl Alcohol, Lauryl alcohol, ethoxylated; lauryl polyethylene glycol ether; alpha-Dodecyl-omega-hydroxy-polyoxyethylene; PolyethyleneGlycols, monododecyl ether; Dodecanol ethoxylate; Dodecanol, polyethoxylated; Dodecyl poly(oxyethylene)ether; Lauromacrogol; Lauryl poly(oxyethylene)ether; Oxyethylenated dodecyl alcohol; Poly(ethylene oxide)dodecyl ether; alpha-dodecyl-omega-hydroxy-Poly(oxy-1,2-ethanediyl); Poly(oxyethylene)monolauryl ether; Polyethoxylated dodecanol; Polyethylene glycol dodecyl ether; Polyethylene glycol lauryl ether; Polyoxyethylene dodecanol; Polyoxyethylene lauric alcohol; and Polyoxyethylene lauryl alcohol; 3,6,9,12,15,18,21,24,27-Nonaoxanonatriacontan-1-ol; Dodecyl alcohol, ethoxylated; Laureth 4 [USAN]; Laureth 9 [USAN]; Laureth-11; Lauromacrogol 400 [INN]; PEG-11 Lauryl ether; Polidocanol, 40L (polyether); Actinol L 7; Actinol L3; Adeka Carpol M 2; Adeka Carpol MBF 100; Adekatol LA 1275; Aethoxysklerol; Akyporox RLM 160; Akyporox RLM 22; Akyporox RLM 230; Akyporox RLM 40; Aldosperse L 9; Alkasurf LAN 1; Alkasurf LAN 3; Arapol 0712; Atlas G 2133; Atlas G 3705; Atlas G 3707; Atlas G 4829; Atlas G-2133; Atlas G-3705; B 205; BASE LP 12; BL 9; BL 9 (polyglycol); Base LP 12; Brij™22; Brij™ 23; Brij™ 30; Brij™ 30ICI; Brij™ 30SP; Brij™ 35; Brij™ 35L; Brij™36T; CCRIS 3397; Calgene 40L; Carsonol L 2; Carsonol L 3; Chemal LA 23; Chimipal AE 3; Cimagel; Conion 275-100; Conion 275-20; Conion 275-30; Conion 275-80; Conion 2P80; Dodecyl alcohol polyoxyethylene ether; Du Pont WK; Ethosperse LA 12; Ethosperse LA 23; G 3707; Glycols, polyethylene, monododecyl ether; HSDB 4351; Hydroxypolyethoxydodecane; LA (Alcohol); LA 7; Laureth; Laureth 9; Lipal 4LA; Lubrol 12A9; Lubrol PX; Marlipal 1217; Mergital LM 11; NCI-C54875; Newcol 1203; Nikkol BL; Noigen ET 160; Noigen ET 170; Noigen YX 500; Noniolite AL 20; Pegnol L 12; Poly(oxy-1,2-ethanediyl), alpha-dodecyl-omega-hydroxy-; Polyethylene glycol monododecyl ether; Polyethylene glycol monododecyl ether, the name is followed by a; number (400) corresponding approximately to the average molecular; mass of the polyethylene glycol portion; Polyethylene glycol monolauryl ether; Polyoxyethylene lauryl ether; Rokanol L; Romopal LN; Simulsol P 23; Simulsol P 4; Siponic L; Slovasol S; Standamul LA 2; Stmer 135; Surfactant WK; Texofor B 9; Thesat; Thesit; alpha-Dodecyl-omega-hydroxypoly(oxy-1,2-ethanediyl); or alpha-Dodecyl-omega-hydroxypoly(oxyethylene).

Other Brij™ polyoxyethylene alkyl ethers include: Brij™ 30 polyoxyethylene (4) lauryl ether $CH_3(CH_2)_{10}CH_2(OCH_2CH_2)_nOH$, n~4); Brij™ 52, polyoxyethylene (2) cetyl ether $(C_{16}H_{33}(OCH_2CH_2)nOH$, n~2); Brij™ 56 polyoxyethylene (10) cetyl ether $(C_{16}H_{33}(OCH_2CH_2)nOH$, n~10); Brij™ 58, polyoxyethylene (20) cetyl ether $(C_{16}H_{33}(OCH_2CH_2)_nOH$, n~20); Brij™ 72 polyoxyethylene (2) stearyl ether, $(C_{18}H_{37}(OCH_2CH_2)nOH$, n~2); Brij™ 76, polyoxyethylene (10) stearyl ether $(C_{18}H_{37}(OCH_2CH_2)nOH$, n~10); Brij™ 78 polyoxyethylene (20) stearyl ether $(C_{18}H_{37}(OCH_2CH_2)nOH$, n~20); Brij™ 92, polyoxyethylene (2) oleyl ether $(C_{18}H_{35}(OCH_2CH_2)nOH$, n~2); Brij™ 93, polyoxyethylene (2) oleyl ether; $(C_{18}H_{35}(OCH2CH2)nOH$, n~2); Brij™ 97, polyoxyethylene (10) oleyl ether $(C_{18}H_{35}(OCH_2CH_2)nOH$, n~10); Brij™ 98, polyoxyethylene (20) oleyl ether $(C_{18}H_{35}(OCH_2CH_2)_nOH$, n~20); Brij™ 700, Polyoxyethylene (100) stearyl ether, $C_{18}H_{37}(OCH_2CH_2)_{21}OH$, n~100; and Brij™ 721, Polyoxyethylene (21) Stearyl Ether $(C_{18}H_{37}(OCH_2CH_2)_nOH$, n~21).

The polyoxyethylene alkyl ether, if present, may be present at a concentration that does not significantly decrease the sensitivity of future assays. The concentration of polyoxyethylene alkyl ether may, in certain embodiments, be decreased during sample processing, e.g., by diluting the polyoxyethylene alkyl ether using neutralization buffer or by addition of a diluent, e.g., buffer or water to the protein extract prior to use.

Depending on the strength of the polyoxyethylene alkyl ether used and the pH of the extraction buffer, the polyoxyethylene alkyl ether may be present in the extraction buffer at a concentration (v/v) of about 0.05% to about 0.1%, of about 0.1% to 0.5%, of about 0.5% to about 1%, of about 1% to about 5%, of about 5% to about 10%, or of about 10% to about 20%.

In a preferred embodiment, a polyoxyethylene alkyl ether, e.g. Brij™35, is present in the extraction reagent at a concentration (v/v) of about 2% to about 10%. In other embodiments, said polyoxyethylene alkyl ether is present in the neutralization reagent. In still other embodiments, said polyoxyethylene alkyl ether is present in both the extraction and neutralization reagents.

In other preferred embodiments, the extraction reagent and/or neutralization reagent comprises other non-ionic detergents in addition to the polyoxyethylene alkyl ether. The non-ionic detergents could either be present in the extraction reagent or the neutralization reagent, or in both the extraction reagent and the neutralization reagent. In certain embodiments, the non-ionic detergent employed may be nonidet P-40, n-octylglucoside, a TRITON™ detergent such as TRITON™ X-100, octyl β-thioglucopyranoside, a TWEEN™ detergent such as TWEEN-20, or NP-40). Depending on strength of the detergent used, the detergent may be present in the extraction buffer or the neutralizing buffer at a concentration of about 0.01 M to about 0.05 M, about 0.05M to about 0.1 M, 0.1 M to about 0.2 M, about 0.2 M to about 0.5 M, about 0.5 M to about 1.0 M, about 1.0 M to about 2.0 M, about 2.0 M to about 4.0 M, or about 4.0 M to about 8.0 M. Further detergents that may be employed in the instant methods are listed in columns 7 and 8 of U.S. Pat. No. 6,488,671, which patent is incorporated herein by reference in its entirety.

Exemplary detergents and their concentrations in a subject neutralizing and/or extraction reagent include: Triton X-100: about 0.1% to about 10%, e.g., about 1%, NP40: about 0.1% to about 10%, e.g., about 1% and Tween-20: about 0.1% to about 10%, e.g., about 1%, weight/vol.

In preferred embodiments, the extraction reagent and/or the neutralization reagent comprises a polyoxyethylene alkyl ether in combination with other non-ionic detergents. The polyoxyethylene alkyl ether may be a Brij™ surfactant and may be combined with one or both Tween™ detergent or Trition™ detergent. In certain preferred embodiments, the Brij™ surfactant is Brij™35 in combination with one or more of the following non-ionic detergents: Tween™-20, about 0.1% to about 10%, e.g. about 2%; or Trition™ X-100, about 0.1% to about 10%, e.g. about 2%.

In certain embodiments, the extraction reagent may contain no significant amount of denaturant. However, in other embodiments, in addition to having a pH of at least 10.0 and a polyoxyethylene alkyl ether such as Brij™35, the extraction reagent may also contain a denaturant, e.g., an ionic detergent such as sodium dodecyl sulphate (SDS) or sarcosyl, or a chaotrophic agent such as urea. In these embodiments, the denaturant, if present, may be present at a concentration that does not significantly decrease the sensitivity of future assays. The concentration of denaturant may, in certain embodiments, be decreased during sample processing, e.g., by diluting the denaturant using neutralization buffer or by addition of a diluent, e.g., buffer or water to the protein extract prior to use. The denaturant may also be present alone, in the absence of polyoxyethylene alkyl ether Depending on strength of the denaturant used and the pH of the extraction buffer, the denaturant may be present in the extraction buffer at a concentration of about 0.01 M to about 0.05 M, about 0.05M to about 0.1 M, 0.1 M to about 0.2 M, about 0.2 M to about 0.5 M, about 0.5 M to about 1.0 M, about 1.0 M to about 2.0 M, about 2.0 M to about 4.0 M, or about 4.0 M to about 8.0 M. Denaturant, if present in the extraction reagent, may be present at a concentration that is well below the concentration of denaturant typically employed to denature protein. In other words, the extraction reagent may contain denaturant at a concentration that allows detection of a protein using a capture agent for that protein, after producing a protein extract according to the subject methods. The concentration of denaturant employed is generally sufficient to produce a protein extract containing proteins that are readily detectable in a binding assay that employs a capture agent, e.g., in an antibody detection assay.

Exemplary denaturants and their concentrations in a subject extraction reagent: sodium dodecyl sulphate (SDS): about 0.01% to about 2%, e.g., 0.05%, sarkosyl: about 0.01% to about 5%, e.g., 0.5%, guanidine: about 0.1 M to about 6 M, e.g., about 0.5M and urea: about 0.1 M to about 8 M, e.g., about 0.5 M, weight/vol.

SDS is typically employed to denature proteins at a concentration of 0.1% to 0.5%, sarkosyl is typically employed to denature proteins at a concentration of 2% w/v, urea is typically employed to denature proteins at a concentration of 2 M to 8 M, guanidine hydrochloride is typically employed to denature proteins at a concentration of 3 M to 8 M, N-cetyl trimethylammonium chloride is typically employed to denature proteins at a concentration of 5% w/v, and N-octylglucoside is typically employed to denature proteins at a concentration of 2%, w/v (See Protein purification Handbook, Amersham Pharmacia Biotech, p. 71 (1999)).

The subject protein extract reagent may contain other components e.g., salt ion chelators, protease inhibitors, etc., in addition to the above-recited components.

The protein extraction reagent may be a liquid or solid composition and may, in certain embodiments, contain a combination of different denaturants.

Denaturants that may be employed in the instant extraction buffer are generally strong denaturants and include but are not limited to: chaotrophic agents (e.g., urea, guanidine hydrochloride, or a thiocyanate salt such as sodium thiocyanate or guanidinium thiocyanate, sodium iodide, sodium perchlorate and the like; see K. Hamaguchi et al., Proc. Natl. Acad. Sci. 62: 1129-1136, 1962) and ionic detergents (e.g., sodium dodecyl sulfate (SDS), sarcosyl or N-cetyl trimethylammonium chloride), including cationic, anionic and zwitterionic detergents (such as CHAPS or CHAPSO). Further denaturants that may be employed in the instant methods are listed in columns 7 and 8 of U.S. Pat. No. 6,488,671, which patent is incorporated herein by reference in its entirety.

In certain embodiments, a weak denaturant such as LiCl, $LiClO_4$, LiBr, $CaCl_2$ or NaCl is not employed as a denaturant in the extraction buffer, although such a compound may be present in a extraction buffer or protein extract in addition to a denaturant listed in the previous paragraph.

As noted above, the extraction reagent is contacted with (e.g., combined or mixed with) fixed or unfixed cells. In certain embodiments, a cellular sample containing cells (e.g., a transport medium containing fixed cells) may be directly added to the extraction reagent. In other embodiments, the cells may be isolated from the cellular sample (e.g., by sedimentation, centrifugation, filtration or affinity methods), prior to their addition to the protein extraction reagent. Cells may be washed or contacted with other reagents prior to their addition to the extraction reagent.

All or a portion of the available fixed or unfixed cells may be combined with the extraction reagent. For example, in certain embodiments, a portion of cells may be employed in a cytology test and a portion of the cells may be contacted with the extraction reagent to produce the intermediate composition. The cells and extraction reagent may be combined and maintained under a suitable temperature (e.g., on ice, at about room temperature or at about 37° C.) and for a suitable time (e.g., from 10 seconds to 24 hr) to produce the intermediate composition. In certain embodiments, the neutralizing reagent is contacted with the intermediate composition immediately after the cells have been contacted with the extraction reagent.

Neutralizing Reagent

The neutralizing reagent employed in the instant methods has a pH that is sufficient to neutralize the pH of the intermediate composition discussed above, upon contact with the intermediate composition. In other words, the neutralizing reagent has a pH that is sufficient to neutralize the pH of the intermediate composition discussed above when the neutralizing reagent is mixed with the intermediate composition. As will be described in greater detail below, the neutralizing reagent may, in certain embodiments, contain a polyoxyethylene alkyl ether or other non-ionic detergent or mixture of detergents.

The pH of the neutralizing reagent is sufficient to neutralize the intermediate composition made by contacting fixed or unfixed cells with a subject extraction reagent. Depending upon the pH of the extraction reagent and whether buffers are employed, the pH of the neutralizing reagent may be between pH 4.0 to pH 8.0. In certain embodiments, the neutralizing reagent may have a pH of about pH 4.0 to about pH 4.5, pH 4.5 to about pH 5.0, pH 5.0 to about pH 5.5, pH 5.5 to about pH 6.0, pH 6.0 to about pH 6.5, pH 6.5 to about pH 7.0 or pH 7.0 to about pH 7.5. Neutralizing reagent may be made using any suitable source of hydrogen ions, e.g., hydrochloric acid or acetic acid, for example. In certain embodiments, the neutralizing reagent may have a pH of less than pH 4.0.

The neutralizing reagent may be buffered or not buffered. If the neutralizing reagent is buffered, then the neutralizing reagent may be buffered using any buffer having a $pK_a$ of about 6 to about 8, e.g., tris, hepes or tricine, for example. In certain preferred embodiments, the neutralizing reagent comprises 2M Tris-HCl, pH about pH 6.0.

In some preferred embodiments, the amount or pH of the neutralization reagent necessary to bring the sample to the target pH, e.g. pH of about pH 7.0 to 8.5, is pre-determined empirically prior to addition of the neutralization reagent. In such embodiments, the empirically-determined neutralization reagent is added to the cellular sample. In other embodiments, following addition of the neutralization reagent, the pH of the neutralized sample is measured. After such measurement step, the pH is adjusted, if necessary, to achieve the targeted neutral pH.

In other embodiments the neutralization reagent comprises one or more, or mixture of: HEPES, Triton™ X-100, NaCl, glycerol and EGTA. An exemplary neutralization reagent comprises about 50 mM HEPES, pH about pH 7.5, about 1.1% Triton™X-100, about 150 mM NaCl, about 10% glycerol, and about 1 mM EGTA. Other exemplary neutralization buffer comprises: about 20 mM Tris, pH 8, about 2% BSA, about 1% Triton™X-100, about 2% Tween™-20, about 0.2% Sarcosine, about 250 mM NaCl, and about 50 mM EDTA (or EGTA).

As noted above, either the extraction reagent and/or the neutralizing reagent may contain a non-ionic detergent or surfactant including, but not limited to, a polyoxyethylene alkyl ether of the formula $CH_3(CH2)_{n1}CH_2(OCH_2CH_2)_{n2}OH$. Exemplary polyoxyethylene alkyl ethers are Brij™ surfactants including one or more: Brij™ 35, polyoxyethylene (23) lauryl ether $(CH_3(CH_2)_{10}CH_2(OCH_2CH_2)_nOH$, n~23); Brij™ 30 polyoxyethylene (4) lauryl ether $(CH_3(CH_2)_{10}CH_2(OCH_2CH_2)_nOH$, n~4); Brij™ 52, polyoxyethylene (2) cetyl ether $(C_{16}H_{33}(OCH_2CH_2)nOH$, n~2); Brij™ 56 polyoxyethylene (10) cetyl ether $(C_{16}H_{33}(OCH_2CH_2)nOH$, n~10); Brij™ 58, polyoxyethylene (20) cetyl ether $(C_{16}H_{33}(OCH_2CH_2)_nOH$, n~20); Brij™ 72 polyoxyethylene (2) stearyl ether, $(C_{18}H_{37}(OCH_2CH_2)nOH$, n~2); Brij™ 76, polyoxyethylene (10) stearyl ether $(C_{18}H_{37}(OCH_2CH_2)nOH$, n~10); Brij™ 78 polyoxyethylene (20) stearyl ether $(C_{18}H_{37}(OCH_2CH_2)nOH$, n~20); Brij™ 92, polyoxyethylene (2) oleyl ether $(C_{18}H_{35}(OCH_2CH_2)nOH$, n~2); Brij™ 93, polyoxyethylene (2) oleyl ether; $(C_{18}H_{35}(OCH2CH2)nOH$, n~2); Brij™ 97, polyoxyethylene (10) oleyl ether $(C_{18}H_{35}(OCH_2CH_2)nOH$, n~10); Brij™ 98, polyoxyethylene (20) oleyl ether $(C_{18}H_{35}(OCH_2CH_2)_nOH$, n~20); Brij™ 700, Polyoxyethylene(100) stearyl ether, $C_{18}H_{37}(OCH_2CH_2)_{21}OH$, n~100; or Brij™ 721, Polyoxyethylene (21) Stearyl Ether $(C_{18}H_{37}(OCH_2CH_2)_nOH$, n~21).

Depending on the strength of the polyoxyethylene alkyl ether used and the pH of the extraction buffer, the polyoxyethylene alkyl ether may be present in the extraction buffer at a concentration (v/v) of about 0.05% to about 0.1%, of about 0.1% to 0.5%, of about 0.5% to about 1%, of about 1% to about 5%, of about 5% to about 10%, or of about 10% to about 20%.

In certain embodiments, the non-ionic detergent employed may be nonidet P-40, n-octylglucoside, a TRITON™ detergent such as TRITON™ X-100, octyl β-thioglucopyranoside, a TWEEN™ detergent such as TWEEN-20, or NP-40. Depending on strength of the detergent used, the detergent may be present in the extraction buffer or the neutralizing buffer at a concentration of about 0.01 M to about 0.05 M, about 0.05M to about 0.1 M, 0.1 M to about 0.2 M, about 0.2 M to about 0.5 M, about 0.5 M to about 1.0 M, about 1.0 M to about 2.0 M, about 2.0 M to about 4.0 M, or about 4.0 M to about 8.0 M. Further detergents that may be employed in the instant methods are listed in columns 7 and 8 of U.S. Pat. No. 6,488,671, which patent is incorporated herein by reference in its entirety. In certain embodiments, the detergent may be present in both the extraction and the neutralizing buffer.

Exemplary detergents and their concentrations in a subject neutralizing and/or extraction reagent include: Triton X-100: about 0.1% to about 10%, e.g., about 1%, NP40: about 0.1% to about 10%, e.g., about 1% and Tween-20: about 0.1% to about 10%, e.g., about 1%, weight/vol.

As noted above, the polyoxyethylene alkyl ether or other non-ionic detergent could be present alone, in combination, or not present in the neutralization reagent. The polyoxyethylene alkyl ether may be a Brij™ surfactant and may be combined with one or both Tween™ detergent or Trition™ detergent. In certain preferred embodiments, the Brij™ surfactant is Brij™35 in combination with one or more of the following non-ionic detergents: Tween™-20, about 0.1% to about 10%, e.g. about 2%; or Trition™ X-100, about 0.1% to about 10%, e.g. about 2%.

As noted above, the neutralizing reagent is contacted with (e.g., combined or mixed with) the intermediate composition to produce a protein extract having a neutral pH (i.e., a pH in the range of about pH 6.5 to about pH 8.0, e.g., in the range of about pH 7.0 and about pH 7.8). The protein extract further contains protein from fixed or unfixed cells, a polyoxyethylene alkyl ether at a concentration listed above, and in certain embodiments, a buffer for maintaining the protein extract in a particular pH range and/or additional non-ionic detergent. If a denaturant is added to the fixed or unfixed cells, the protein extract may further contain that denaturant. The pH, choice of detergent and concentration of the detergent employed (and, if a denaturant is employed, the identity and concentration of the denaturant) are sufficient to allow the protein extract to be directly employed in a binding assay to detect proteins present in the protein extract.

Neutralization of the cell extract may also be carried out by passing the extract through a filter or filter tip that is impregnated with neutralizing reagent. As the extract passes through the filter material, neutralizing reagent is solubilized and the pH of the extract approaches neutrality.

An alternative method for neutralizing the cell extract is to pass the extract through a BioSpin column (BioRad) pre-equilibrated with a solution at neutral pH. The extract may also be placed in a syringe or similar apparatus that contains gel (or filtering material) containing neutralizer and delivered from the syringe by positive pressure.

In certain embodiments, the subject protein extract contain solubilized HPV E6 protein (particularly E6 protein from oncogenic strains of HPV) that is accessible to and readily detectable by a capture agent without further treatment of the protein extract (e.g., without further addition of denaturant, pH changes or heating). The protein extract may also contain solubilized or insoluble membranes, proteins other than HPV E6 protein, and other cellular contents such as DNA, RNA, carbohydrates, etc. Other contaminants such as those derived from mucal contamination of the original cellular sample may also be present. The components of the protein extract generally do not contain whole (i.e., cytologically intact) cells.

The protein extract may be used immediately, or stored, e.g., in frozen form, before use.

In particular embodiments, the protein extracts produced by the methods set forth above may be employed in protein detection methods, which methods are described in greater detail below.

As would be apparent from the above, a variety of different denaturants, detergents, buffers, pHs and component concentrations may be employed in the reagents described above. The optimal denaturant, detergent, buffer or pH, or component concentration in any reagent is readily determined using routine methods.

After neutralization of the cell extract, E6 protein may be concentrated from the cell extract by incubating the extract with particles containing binder for the E6. The binder may comprise PDZ, E6 Associated Protein (E6AP) or fragments thereof, or E6 Binding Protein (E6BP) or fragments thereof. After E6 is captured by the particles, the particles are washed and E6 is then released from the particles by incubation with buffer at pH greater than 10. The particles are separated from the eluting solution and the remaining solution is then neutralized by the procedures described previously. Alternatively, E6 protein may be detected without release from the capture particles.

Further detergents that may be employed in the instant methods are listed in columns 7 and 8 of U.S. Pat. No. 6,488, 671, which patent is incorporated herein by reference in its entirety. In certain embodiments, the detergent may be present in both the extraction and the neutralizing buffer.

In still other embodiments, the sample may be diluted following the neutralization step. An exemplary diluent may include: about 50 mM HEPES, pH about pH 7.5, about 1.1% Triton™X-100, about 150 mM NaCl, about 10% glycerol, and about 1 mM EGTA. Another exemplary diluent may include: about 50 mM Tris, pH 8.2, about 2% BSA, about 2% Triton™X-100, about 0.1% Sarcosine, about 150 mM NaCl, and about 50 mM EDTA (or EGTA).

Protein Detection Methods

The protein extract made by the methods discussed above may be employed directly or indirectly (i.e., after addition of further reagents) in a methods in which the presence of one or more proteins in the protein extract is assessed. The protein detection methods generally involve a capture agent that specifically binds to a protein. The identity of the proteins to be detected may be of known (i.e., pre-determined) or unknown identity at time of performing the method.

Proteins that may be detected using the subject protein detection methods include proteins that are diagnostic markers a disease or condition, e.g., cancer, inflammatory disease, or infection by virus, bacteria or fungus, for example. In certain embodiments, a protein detected using the subject methods is not routinely detectable unless the subject protein extraction methods are employed.

Exemplary proteins that may be detected using the instant methods include proteins that are encoded by an infectious agent, such as human papilloma virus (HPV). In particular embodiments, the instant methods may be employed to detect the E6 protein of HPV, a protein that has proven difficult or impossible to detect in protein extracts made from fixed cells by other methods.

In general terms, protein detection methods are very well known in the art and include binding assays, i.e., assays in which binding between a protein and a capture agent for the protein are detected. Such assays include immunoassays, i.e., binding assays that employ an antibody that specifically binds to a protein, including, but not limited to, competitive and non-competitive assay systems using techniques such as western blots, radioimmunoassays, ELISA (enzyme linked immunosorbent assay), "sandwich" immunoassays, enzyme immunoassays, cytometric bead arrays (CBA), multiplexed bead assays, western blot, immunohistochemistry assays, immunocytochemistry assays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below. Capture and release using E6 BP or AP peptides, specific antibodies, or PDZ domain proteins could be used as a post-extraction, pre-assay method to concentration HPV E6. Alternatively, a dual monoclonal antibody format could be employed.

Immunoprecipitation protocols generally involve producing a protein extract, adding a capture agent, e.g., an antibody, to the protein extract and incubating the protein extract and capture agent for a suitable period of time and temperature. The capture agent is then bound to a solid support, e.g., an affinity substrate such as beads linked to protein A and/or protein G, and the mixture is incubated and washed. The solid support is resuspended in sample buffer and the protein of interest may be detected by western blotting, for example.

ELISAs may involve preparing a protein extract, linking the protein extract to a solid support (e.g., a well of a multi-well microtiter plate), contacting the support-bound protein extract with a capture agent, e.g., an antibody, and detecting binding between the capture agent and the protein. In certain ELISA methods, the capture agent may be detectably labeled with a detectable moiety such as an enzymatic substrate (e.g., horseradish peroxidase or alkaline phosphatase) prior to contacting the capture agent with the support-bound protein extract. In other embodiments, however, binding of the capture agent to the protein extract may be detected by a detectably second capture agent (e.g., a second antibody) that binds to the capture agent contacted with the protein extract.

In other ELISA assays, the capture agent may be linked to a solid support, and the protein extract is contacted with the solid support-bound capture agent. Binding of a protein in the protein extract to the solid-support antibody may be detected using a second capture agent for the protein. Such "sandwich assays" are well known in the art.

In other assays, binding between a capture agent and the protein may occur in solution prior to surface immobilization of the capture agent.

In particular, the instant methods may be employed to detect the E6 protein from oncogenic strains of HPV. In these embodiments, the capture agent employed in the detection method may be, for example, an antibody or a polypeptide comprising a PDZ domain that binds to a PDZ ligand (i.e., a binding site for a PDZ domain) contained in the E6 protein. For example, the instant E6 detection binding method may employ a PDZ domain-containing protein that contains the second PDZ of MAGI-1, or the PDZ domain of DLG or TIP1, etc, as described in published application US 20040018487 (published on Jan. 29, 2004) and incorporated herein by reference in its entirety. Exemplary PDZ domain-containing proteins and PDZ domain sequences are shown in TABLE 2 and EXAMPLE 4 of application US 20040018487. The term "PDZ domain" also encompasses variants (e.g., naturally occurring variants) of the sequences (e.g., polymorphic variants, variants with conservative substitutions, and the like) and domains from alternative species (e.g. mouse, rat). Typically, PDZ domains are substantially identical to those shown in U.S. patent application Ser. No. 09/724,553 which is herein incorporated by reference, e.g., at least about 70%, at least about 80%, or at least about 90% amino acid residue identity when compared and aligned for maximum correspondence. It is appreciated in the art that PDZ domains can be mutated to give amino acid changes that can strengthen or weaken binding and to alter specificity, yet they remain PDZ domains (Schneider et al., 1998, Nat. Biotech. 17:170-5). Unless otherwise indicated, a reference to a particular PDZ domain (e.g. a MAGI-1 domain 2) is intended to encompass the particular PDZ domain and HPV E6-binding variants thereof. In other words, if a reference is made to a particular PDZ domain, a reference is also made to variants of that PDZ domain that bind oncogenic E6 protein of HPV, as described below. In this respect it is noted that the numbering of PDZ domains in a protein may change. For example, the MAGI-1 domain 2 (of amino acid sequence PSELKGKFIHTKLRKSSRGFGFTV-VGGDEPDEFLQIKSLVL DGPAALDGKMETGDVI VSVNDTCVLGHTHAQWKIFQSIPIGAS-VDLELCRGYPLPFDPDDPN), as referenced herein, may be referenced as MAGI-1 domain 1 in other literature. As such, when a particular PDZ domain of a protein is referenced in this application, this reference should be understood in view of the sequence of that domain, as described herein, particularly in the sequence listing Table 2 of Application US 20040018487, shows the relationship between the sequences of the sequence listing and the names and Genbank accession numbers for various domains, where appropriate. As used herein, the term "PDZ protein" refers to a naturally occurring protein containing a PDZ domain. Exemplary PDZ proteins include CASK, MPP1, DLG1, DLG2, PSD95, NeDLG, TIP-33, SYN1a, TIP-43, LDP, LIM, LIMK1, LIMK2, MPP2, NOS1, AF6, PTN-4, prIL16, 41.8kD, KIAA0559, RGS12, KIAA0316, DVL1, TIP-40, TIAM1, MINT1, MAGI-1, MAGI-2, MAGI-3, KIAA0303, CBP, MINT3, TIP-2, KIAA0561, and TIP-1. As used herein, the term "PDZ-domain polypeptide" refers to a polypeptide containing a PDZ domain, such as a fusion protein including a PDZ domain sequence, a naturally occurring PDZ protein, or an isolated PDZ domain peptide. A PDZ-domain polypeptide may therefore be about 60 amino acids or more in length, about 70 amino acids or more in length, about 80 amino acids or more in length, about 90 amino acids or more in length, about 100 amino acids or more in length, about 200 amino acids or more in length, about 300 amino acids or more in length, about 500 amino acids or more in length, about 800 amino acids or more in length, about 1000 amino acids or more in length, usually up to about 2000 amino acids or more in length, about 50-2000 amino acids in length, about 50-1500 amino acids in length, about 50-1000 amino acids in length, about 60-1000 amino acids in length, about 70-1000 amino acids in length. PDZ domain peptides are usually no more than about 200 amino acids (e.g. 50-200 amino acids, 60-180 amino acids, 80-120 amino acids, or 90-110 amino acids), and encode a PDZ domain.

Antibodies suitable for detecting the E6 protein of HPV are described in 20050142541 (published on Jun. 30, 2005), for example. Detailed methods for identifying the E6 protein from oncogenic strains of HPV are found in published U.S. patent application US20040018487, which methods are incorporated herein in their entirety. These published methods are readily adapted for employment in the instant methods.

In certain embodiments, an anti-E6 antibody may be bound to a solid support, and a protein extract produced by the subject methods is contacted with the solid support bound antibody. Such solid supports are well known in the art and may include but are not limited to: colloidal gold particles, chemiluminescent particles, dyed latex particles, or SERS Raman particles, e.g. silica-coated gold or silver cores with reporter dyes. In certain embodiments, an anti-E6 antibody may be conjugated to a fluorescent label.

Binding of oncogenic E6 protein in the protein extract may be detected using a PDZ domain-containing protein. In other embodiments, a PDZ domain-containing protein may be bound to a solid support, and a protein extract produced by the subject methods is contacted with the solid support bound PDZ domain-containing protein. Binding of oncogenic E6 protein in the protein extract may be detected using an anti-E6 antibody. In alternative methods, binding between the antibody of PDZ domain-containing protein may occur in solution (i.e., in the absence of binding of either the antibody or PDZ domain-containing protein to a solid support), and, after binding, the antibody or PDZ domain-containing protein may be bound a solid support (e.g., beads or the like such as those described above). In these embodiments, the PDZ domain-containing protein may be a fusion protein having an affinity domain that binds to the solid support. The presence of the E6 protein can be detected using a second capture agent that recognizes the E6 protein.

In preferred embodiments, lateral flow (LF) assays, immunochromatographic assays, dipstick tests, or flow-through immunoassays are employed to detect extracted captured E6 protein. In preferred embodiments, a lateral flow (LF) strip comprising a "capture-zone" of PDZ-domain-containing proteins is placed into a vial or well containing extracted sample, to which has been added a second capture agent such as anti-HPV E6 monoclonal antibodies (mAb) conjugated to gold particles. The gold particles and sample are then allowed to migrate up the strip via capillary action. An absorbent pad may be attached to the distal end to facilitate flow of the liquid up the strip. During the migration of the sample up the strip, PDZ-domain proteins in the capture zone may bind to the E6 protein. If binding of gold-conjugated mAb's occurred in solution, the anti-E6-gold conjugate could bind to the PDZ domain protein. Alternatively, the E6 protein could bind the PDZ domain protein followed by capture of the E6 gold conjugate. Under either scenario, successful capture may result in the formation of a visible and detectable line on the LF strip.

In preferred embodiments, a cytometric bead array (CBA) is employed to aid the detection of the captured E6 protein. A CBA, also known as a multiplexed bead assay, is a series of spectrally discrete particles that can be used to capture and quantitate soluble analytes. The analyte is then measured by detection of a fluorescence-based emission and flow cytometric analysis. The Becton Dickinson (BD)™ CBA generates data comparable to ELISA-based assays, but in a "multiplexed" or simultaneous fashion. As with any sandwich format assay, the calculation of the concentration of unknown analyte occurs generally through the use of known standards and plotting unknowns against a standard curve.

Instruments useful for detecting the captured E6 protein are well-known in the art. For example, a reflectometer instrument or UMM reader may be used to detect the resulting line on the LF strip. Alternatively, a fluorometric reader may be employed if fluorescently-labeled anti-E6 mabs are used to capture the E6 protein. Devices in which detector particles are incorporated as an inherent part of the device itself could also be used. Alternatively, the invention extraction process could produce an input sample consisting of an E6 moeity alone or complexed with specific antibodies, peptides or proteins (either attached or non-attached to particles). Such input sample could be introduced into a specific capture or non-specific membrane-based flow though detection device and subsequently detected by enzymatic or particle-based systems or amplified detection systems.

A number of approaches could be employed to enhance signal detection. One such approach would employ enzyme conjugated (e.g. horse-radish peroxidase (HRP) or alkaline phosphatase (AP)) monoclonal antibodies (mAbs) conjugated to gold particles in conjunction with a precipitating substrate. Antibodies with multiple biotins followed by streptavidin gold particles could also result in amplified signal. Biotin tyramide could be used to deposit more biotin around the test line, followed by streptavidin-conjugated gold for amplification and detection. Alternatively, signal enhancement could result from using a two-tier process involving a primary particle consisting of biotin and a specific niab-co-conjugated gold particle (or fluorescently-labeled particle) followed by a secondary particle conjugated with streptavidin. The primary particle could be a specific E6 iteratively-tagged particle followed by an anti-tag secondary particle. The primary particle could also be a cocktail of antibodies capable of reacting with E6 proteins deriving from some, many or all oncogenic strains of HPV and/or with one or more epitopes of the E6 protein. Such cocktail of antibodies could be biotinylated, conjugated to a solid support (e.g. gold particle) or fluorescently-labeled; and many of the methods described herein could be used in conjunction with such cocktail to detect the E6 protein.

In certain embodiments, the active ingredient in the extraction buffer may be increased in order to enhance solubilization of the clinical specimen. Such enhanced solubilization could obviate the need to clarify the sample and eliminate a step in the assay. It might also be possible to pellet anti-E6-mAb-gold complexes and reconstitute in a small volume in order to concentrate the sample, thereby enriching the E6 protein and enhancing sensitivity of the assay.

Results obtained from the assay methods described above may be compared to results obtained from suitable controls, e.g., a positive control (in which a protein extract known to contain the protein to which the capture agent binds may be employed) or a negative control (e.g., in which a protein extraction reagent that has not been contacted with a cellular sample may be employed).

Results obtained from the assay methods described above may indicate the presence, absence, or, in certain embodiments, the amount of a protein in a protein extract.

In certain embodiments, the results obtained from the assay methods described above may be communicated back to a remote location, e.g., by telephone, fax, e-mail, mail or any other means. The results may be communicated to the subject or a subject's doctor, for example.

The above protein detection methods may be performed in combination with a different test, such as a cytological test, e.g., a Pap test for identifying cancerous or pre-cancerous cervical cells, or other molecular tests. In these embodiments, the cellular sample may be divided into parts prior to use. The first part may be used in cytological assays and the second part may be used in the above-described methods.

In accordance with the above, certain embodiments of the invention also provide a system for producing a protein extract. The system generally contains: a) a cellular sample containing fixed or unfixed cells; b) an extraction reagent that has a pH of at least about pH 10.0; and c) a neutralizing reagent, where the fixed or unfixed cells, extraction reagent and neutralizing agent may be employed in the above methods to produce a protein extract suitable for use in a binding assay. The extraction reagent and/or the neutralization reagent contains a polyoxyethylene alkyl ether.

Kits

In yet another aspect, the present invention provides kits for practicing the subject methods, e.g., for producing a protein extract from fixed or unfixed cells, in certain embodiments, for testing for the presence of a protein in the protein extract. The subject kits at least include an extraction reagent that has a pH of at least about pH 10.0, and a neutralizing reagent. The extraction reagent and/or the neutralizing reagent contains a polyoxyethylene alkyl ether. In addition, the kits may include a capture agent for detecting a protein, and, in certain embodiments, reagents (e.g., buffers and detection reagents) for detecting that protein using the capture agent. The above components may be present in separate containers or one or more components may be combined into a single container, e.g., a glass or plastic vial.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Utility

The method and system described above are readily employed in a variety of research and diagnostic methods, including methods of diagnosing a particular disease or condition, or infection by an infections agent, such as a virus or bacteria. In one embodiment, the method is employed as part of a diagnostic for detecting HPV infected cells. Since the presence of oncogenic strains of HPV is associated with cancerous and pre-cancerous cells, the instant methods may be employed to detect cancerous or pre-cancerous cervical cells.

HPV is known to be a causative agent in the following diseases: epidermodysplasia verruciformis (EV), a lifelong skin disorder that results in high risk for skin (e.g., squamocelllar) cancer; cervical neoplasias such as cervical intraepithelial neoplasia (CIN) and invasive cervical carcinoma (ICC); viginal neoplasias such as vaginal intraepithelial neoplasia (VAIN) and vaginal carcinoma (VC); vulval neoplasias such as vulvar intraepithelial neoplasia (VIN) and vulvar carcinoma; penile carcinoma (including Bowenoid papulosis); anal (AC) and perianal carcinomas (PC); oropharyngeal carcinomas (OS); esophageal carcinomas (EC); non-melanoma skin cancers (e.g., basal cell carcinoma-BCC and squamous cell carcinoma-SCC); and melanoma. As such, in one embodiment, the instant methods may be employed as a diagnostic for any of these diseases.

In one embodiment, cells are obtained (e.g., exfoliated or dissected) from a subject and deposited into a liquid medium containing a fixative that, in certain embodiments, may be a transport medium for cytological test. The cells are usually obtained in doctor's office or clinic, the cellular sample is forwarded to and received by a testing facility in which the above-recited protein detection methods and, optionally, cytology assays are performed. Results from the testing are communicated to the subject, in some embodiments via the doctor and an associate thereof.

The subject from which cells are employed may be a mammal, e.g., a dog or cat, a rodent (e.g., mouse, guinea pig, or rat), or primate (e.g., a human, chimpanzee, or monkey). In many embodiments, the subject will be a human, particularly a male or female. In certain embodiments, the subject may show symptoms of HPV infection (e.g., may have warts on one or more parts of the body), may be suspected of being infected by HPV (e.g., may contain cells that are cytologically consistent with such an infection) or may have already tested positive for HPV. In certain embodiments, the subject may have no indication of HPV infection, and the above methods may be employed as part of a routine screen.

In one embodiment, the instant methods may be employed to detect any strain of oncogenic HPV, e.g., HPV 26, HPV 53, HPV 66, HPV 73, HPV 82, HPV 16, HPV 18, HPV 31, HPV 35, HPV 30, HPV 39, HPV 45, HPV 51, HPV 52, HPV 56, HPV 59, HPV 58, HPV 33, HPV 66, HPV 68 or HPV 69, (particularly any of the most prevalent HPV strains, e.g., HPV 16, HPV 18, HPV 31, HPV 33 and HPV 45) by detecting the E6 protein from that strain. In one embodiment, at the point of initiating the instant methods, it is not known if the fixed or unfixed cells contain oncogenic E6 protein or which strain an oncogenic E6 protein is from. If a detection assay indicates the presence of an oncogenic E6 protein in cells, then the identity of the strain of HPV that infected those cells can be determined by other molecular assays, e.g., those that employ antibodies specific to a particular E6 protein or other protein encoded by the virus, or by sequencing viral DNA.

The following examples are offered by way of illustration and not by way of limitation.

EXAMPLES

Example 1

Extraction of Spiked Clinical Samples

Cells transfected with the HPV16 E6 gene (C33A+) were fixed with THINPREP™ medium and added (i.e., "spiked") into portions of the THINPREP™-fixed clinical samples as listed below. The cells were spiked into half of each of five clinical samples (each half clinical sample having 20 million C33A+ cells).

Extraction Scheme:
C33A(+) ThinPrep cells/20M cells per ml
1-20M C33A(+) ThinPrep cells into ½ clinical negative #229 (1.0 ml extraction)
2-20M C33A(+) ThinPrep cells into ½ clinical negative #230 (1.0 ml extraction)
3-20M C33A(+) ThinPrep cells into ½ clinical negative #231 (1.0 ml extraction)
4-20M C33A(+) ThinPrep cells into ½ clinical negative #232 (1.0 ml extraction)
5-20M C33A(+) ThinPrep cells into ½ clinical negative #233 (1.0 ml extraction)
6-20M C33A(+) ThinPrep cells (1.0 ml extraction)

Extraction Reagent:
Triton X-100/Lot 092K0171—(1%=250 ul)
5M NaCl/Lot 5701-53—(0.15M=750 ul)
0.5M Tris Base/Lot 5708-20—(0.1M=5 ml)
0.5M Glycine/Lot 5708-9—(0.1M=5 ml)
10% SDS/Lot 5708-8—(0.05%=125 ul)
8M Urea/Lot 5678-83—(0.25M=781 ul)
Add RO/DI to 20 ml—(8.1 ml)
5N NaOH/Lot A09522—(525 ul)
Add RO/DI to 25 ml—(4.475 ml)
Final pH—11.48
Final formulation: 0.1 M Tris/0.1 M glycine/0.15 M NaCl/1% Triton™X-100/0.05% SDS/0.25 M urea pH 11.48

Protein Extraction Procedure:
1. Add cell suspension to 50 ml centrifuge tube
2. Spin at 3000 rpm for 10-15 minutes
3. Carefully remove supernatant
4. Transfer contents to a 1.5 ml nunc tube
5. Spin at 3000 rpm for 10-15 minutes
6. Carefully remove supernatant
7. Add required quantity of extraction reagent to pellet
8. Re-suspend to break up cell pellet
a. Additives (DTT @ 1:100)
9. Check pH, adjust to 11.5
10. Mix at RT (or appropriate temperature for extraction) for 30 minutes
11. Spin at 14,000 rpm for 10-15 minutes
12. Remove clarified supernatant
13. Add DTT @ 1:100
14. Neutralize to pH 8.0 with 5N HCl and test in ELISA (Neutralize to pH 8.0 with 31.0 ul 5N HCl/1 ml)
100 mM DTT/NR 5701-90/DOM 2/7/05

ELISA Method

1—Coat plate (Nunc 439454 Maxisorp F96/lot 542043) with 5 ug/ml GST-Magi-PDZ (lot 88.18/0.65 ug/ul) in PBS (lot 021405)—100 ul per well
11 ml×5 ug/mid=55 ug×1 ul/0.65 ug=84.6 ul GST-Magi-PDZ
2—Incubate overnight at 4° C.
3—Wash 3× (TBS-Tween) with plate washer
4—Block plate with 250 ul blocking buffer (lot 033005)
5—Incubate for 2 hours 25° C.
6—Wash 3× (TBS-Tween) with plate washer
7—Add 100 ul MBP-E6/lysate sample to appropriate wells
8—Incubate for 1 hour 25° C.
9—Wash 3× (TBS-Tween) with plate washer
10—Add 100 ul of anti-E6 antibody (4C6-2.85 mg/ml—lot 02) @ 5 ug/ml to appropriate well in 2% BSA HNTG buffer (lot 031805B). N-terminus peptide (HPV16E6 lot#PN3952-2) is added to appropriate samples at 10 ug/ml to verify signal specificity (peptide is pre-incubated with the anti-E6 antibody for 45 minutes prior to addition).
11—Incubate for 2 hour 25° C.
12—Wash 3× (TBS-Tween) with plate washer
13—Prepare a 1:5000 dilution of goat anti-mouse IgG-HRP (Jackson G×M IgG-HRP/catalog #115-035-062/lot 60988) in 2% BSA/0.05% Tween 20 buffer (lot 040505).
10.0 ml×1/5000=0.002 ml×1000 ul/ml=2.0 ul goat anti-mouse IgG-HRP
14—Add 100 ul 1:5000 goat anti-mouse IgG-HRP dilution to appropriate wells
(Remove TMB Substrate and place at room temperature)
15—Incubate for 1 hour 25° C.
16—Wash 5× (TBS-Tween) with plate washer
17—Add 100 ul Neogen K-Blue TMB Substrate (lot 041018)
18—Incubate for 30 minutes at 25° C.
19—Add 100 ul Stop Solution (lot 030705) and Read A450

Formulation:
2% BSA/0.05% Tween buffer—(lot 040505)
2% BSA blocker lot 033005 (49.975 ml)
Tween 20 lot A016759301 (0.025 ml)

Results

|  | Sequential (NO peptide) | | | Sequential (N-terminus peptide) | |
| --- | --- | --- | --- | --- | --- |
|  | OD | | Average | Average | OD |
| 20M C33A(+) TP cells in ½ clinical negative #229* | 1.294 | 1.220 | 1.257 | 0.464 | 0.516 0.411 |
| 20M C33A(+) TP cells in ½ clinical negative #230* | 1.140 | 1.103 | 1.122 | 0.631 | 0.630 0.632 |
| 20M C33A(+) TP cells in ½ clinical negative #231* | 1.136 | 1.178 | 1.157 | 0.443 | 0.451 0.434 |
| 20M C33A(+) TP cells in ½ clinical negative #232* | 0.946 | 0.924 | 0.935 | 0.580 | 0.585 0.574 |
| 20M C33A(+) TP cells in ½ clinical negative #233* | 1.288 | 1.169 | 1.229 | 0.843 | 0.843 0.843 |
| 20M C33A(+) TP cells | 1.762 | 1.691 | 1.727 | 0.345 | 0.334 0.356 |
| C33A(+)/2M cells/LB (+ve) | 2.052 | 2.134 | 2.093 | | |
| C33A(−)/2M cells/LB (−ve) | 0.167 | 0.188 | 0.178 | | |
| Anti-4C6 + N-Term (−ve) | 0.056 | 0.062 | 0.059 | | |
| Anti-4C6 (−ve) | 0.106 | 0.115 | 0.111 | | |

*Extraction volume - 1 ml

As can been seen from the results shown in the above table, E6 binding was detected for all spiked clinical samples.

Example 2

Effect of High pH Buffer Plus Additives on MBP-E6 Detection

The example described in FIG. 1 illustrates the effect of buffers of differing composition on the detection of recombinant maltose-binding protein (MBP)-E6 protein. Ordinarily, the extraction buffers described herein would be used to extract protein from cells. Here, however, previously-purified recombinant protein was used in order to optimize conditions. Briefly, the experiments described in FIG. 1A involved suspending the MBP-E6 protein in freshly-prepared extraction buffers differing in additive content and pH. This "extraction" step was followed by a neutralization step in which the pH of the sample was adjusted to a neutral pH. MBP-E6 protein was then detected using a lateral flow assay.

Composition of the Buffers

The buffers used in the experiments described herein were derived from one of two buffers, either a lower pH buffer, "Buffer 1" or a higher pH buffer, "Buffer 2." Buffer 1 (pH of about 11.5) consisted of: about 100 mM Tris/Glycine, about 50 mM Hepes, about 150 mM NaCl, about 1 mM EGTA, about 1.1% Triton™ X-100, and about 0.125-0.14 N NaOH. Buffer 2 (pH of about 12-13) consisted of about 0.1 N NaOH and about 50 mM TriSodium Citrate. Each buffer was then supplemented, or not, with a "low" or "high" amount of the additive indicated in FIG. 1A. The additives in the low-additive buffers had concentrations of about: 0.25M urea; 0.05% SDS; 2% Tween™-20; 2% Brij™ 35 (Sigma); 2% saponin; 2% Tergitol NP 40; or 10 mM EDTA, pH 8. The additives in the high-additive buffers had concentrations of about 2M urea; 0.5% SDS; 4% Tween™-20; 4% Brij™ 35; 4% saponin; 4% Tergitol NP 40; or 50 mM EDTA, pH 8. As indicated above, Buffer 1 had a stock level of 1.1% Triton™X-100, which was used for both low and high samples. For Buffer 2, Triton™ X-100 was at a concentration of 2% (low) or 4% (high).

In most of the examples described herein, the buffers were prepared, including the individual additives, immediately prior to addition to the samples. However, in some cases, the samples were treated first with buffer before one or more additives were introduced into the sample.

Detection of the MBP-E6 Protein

In the experiment depicted in FIG. 1A, 520 pg of MBP-E6 was suspended in 1.03-1.13 ml of the indicated extraction buffer which had been freshly-prepared with the indicated additive. The suspension was then gently mixed (end-over-end) at RT for about 30 minutes. For the neutralization step, the suspension was adjusted to a lower pH (approximately 7.8 to 8) using about 2 M Tris and again rotated at RT for 30 minutes. Approximately 150-200 ul of the sample was analyzed by the lateral flow (LF) assay described herein in order to detect the MBP-E6 recombinant protein.

Description of Lateral Flow (LF) Assay

The lateral flow (LF) assay described herein is also known as an immunochromatographic assay or dipstick assay. In brief, the LF assay here involves the capture of gold-particle-bound viral proteins on a "capture zone" present on an LF stick. Successful capture results in the appearance of a visible and detectable line on the LF strip.

Materials: 20% (w/v) BSA 0.22 µm filtered (Sigma A7906); Colloidal GOld 8G11 (BBI); lateral flow strips, PDZ capture.

Method: 1) About 150-200 µl of sample is placed into duplicate wells in a 96-well plate.

2) About 20 µl 20% BSA is added to each well and mixed with a pipet tip.

3) About 10 µl of 8G11-conjugated colloidal gold is added to each well and mixed with a pipet tip. 8G11 is a monoclonal antibody (mAb) that recognizes HPV16 E6 protein.

4) A LF strip is placed into each well for approximately 120 minutes to permit the sample to migrate up the strip by capillary action. An absorbent pad may be attached to the distal end to facilitate flow of the liquid up the strip. During the sample migration, the HPV 16 E6 protein may bind to the mAb attached to the colloidal gold particles. The E6 protein is also captured by a zone on the LF strip containing multiple PDZ domain bearing proteins capable of recognizing E6 protein. Such capture results in the appearance of a visible and detectable red line on the LF strip.

5) The LF strips are then analyzed by a UMM instrument, which is an instrumented reflectance reader capable of quantitating visible signal output. The values obtained are relative reflectance values.

Results

The example illustrated by FIG. 1 shows that combining certain additives with high pH extraction buffer (Buffer 2, pH 12.9), causes a synergistic effect on the detection of the MBP-E6 protein. For example, when Buffer 1 was compared to Buffer 2 in the absence of additives, it appeared that enhanced pH had no effect on the detection of the recombinant MBP-E6 protein (FIG. 1A, last 4 columns). Certain additives, notably SDS, TWEEN™-20, Brij™ 35 and Tergitol NP40, did increase the detection of MBP-E6 protein even when the comparatively lower pH buffer, Buffer 1, pH 11.5 was used (FIG. 1A). However, when the additives were combined with the higher pH buffer (Buffer 2) the detection of the recombinant protein was greatly increased in the SDS, TWEEN™-20, Triton™ X 100, and Brij™ 35 samples. For example, the detection of the protein in the Triton™ X-100 treated sample jumped from 0 to over ~2.4 UMM reading when the pH was increased. It is thus possible to conclude that combining a high pH with certain of the additives during the "extraction" step exerted a synergistic effect on the detection of the E6 protein.

Figure 1B:
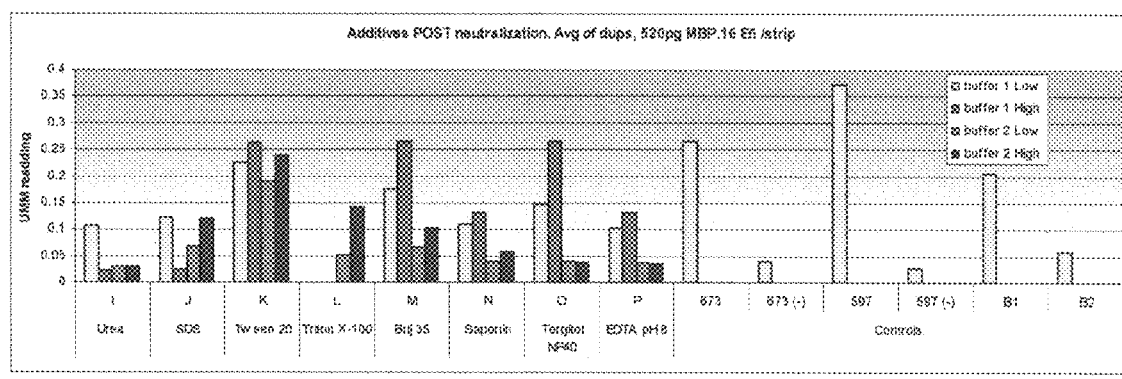
FIG. 1B supports that introduction of additives at the neutralization stage did not have as strong an effect as introduction during the extraction stage on the detection of extracted HPV16 E6 protein.

FIG. 1B describes experiments that were similar to the ones conducted in 1A. However, in FIG. 1B, the additives were introduced to the sample during the neutralization step instead of the earlier "extraction" step. This approach yielded much lower signal intensities than when the additives were introduced during the extraction step. Accordingly, introduction of the additives at the neutralization step is not an optimal approach.

Example 3

Effect of Additives on the Extraction of E6 Protein From Cells

Figure 2:
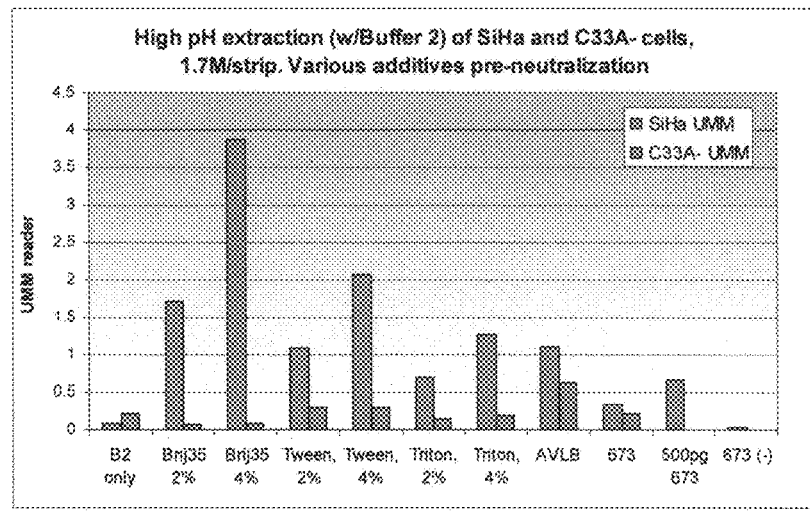
FIG. 2 demonstrates the detection of HPV16 E6 protein extracted from HPV16-expressing SiHa cells using various additives in the extraction reagent.

The example illustrated by FIG. 2 evaluated the effect of different percentages of buffer additives on the extraction of E6 protein from cells. In this example, protein was extracted either from SiHa cells expressing the HPV16 E6 gene or from C33A-cells, which are a non-HPV infected cervical cancer cell line.

Extraction Step

For the extraction step, cell pellets containing about 10 million cells were first removed from a −80° C. freezer and allowed to thaw at RT for about 10 minutes. Then, about 750 µl of Buffer 2, described in Example 2, was added to most of the samples. Additives such as Brij™ 35, Tween™-20, or Triton™X-100 were also introduced to the indicated samples. These additives were present at a final concentration of either 2% or 4% (v/v). As a control, some samples were extracted with Buffer 673, a neutral pH buffer containing 20 mM Tris pH 8, 2% BSA, 1% Triton™-X 100, 2% Tween™-20, 0.2% Sarcosine, 250 mM NaCl, and 50 mM EDTA. The samples were briefly vortexed and then rotated for 30 minutes at RT.

Neutralization Step

For the neutralization step, approximately 140-180 ul of 2M Tris, pH 6.0, was added in order to reduce the pH of each sample to about pH 7.8-8. The volume of Tris, pH 6.0, necessary to neutralize the pH of the samples was previously determined empirically. Following the addition of the Tris and brief vortexing, the samples were rotated at RT for 30 minutes. The samples were then clarified by 10 minutes of centrifugation at 14K rpm. The clarified lysates (approximately 1.09 final volume) were then transferred to a clean tube before being analyzed by the LF assay described in Example 2.

Results

The HPV 16 E6 protein was best detected when Buffer 2 containing 4% Brij™ 35 was used in the extraction step (FIG. 2). In addition, comparison of the signal from the SiHa cells with the HPV E6-negative C33A-cells, indicated that this condition also considerably increased the signal-to-noise ratio of the assay (FIG. 2).

Example 4

Dose Response Detection of HPV-16 E6 Protein After Extraction with 4% Brij™35/Buffer 2

Figure 3:
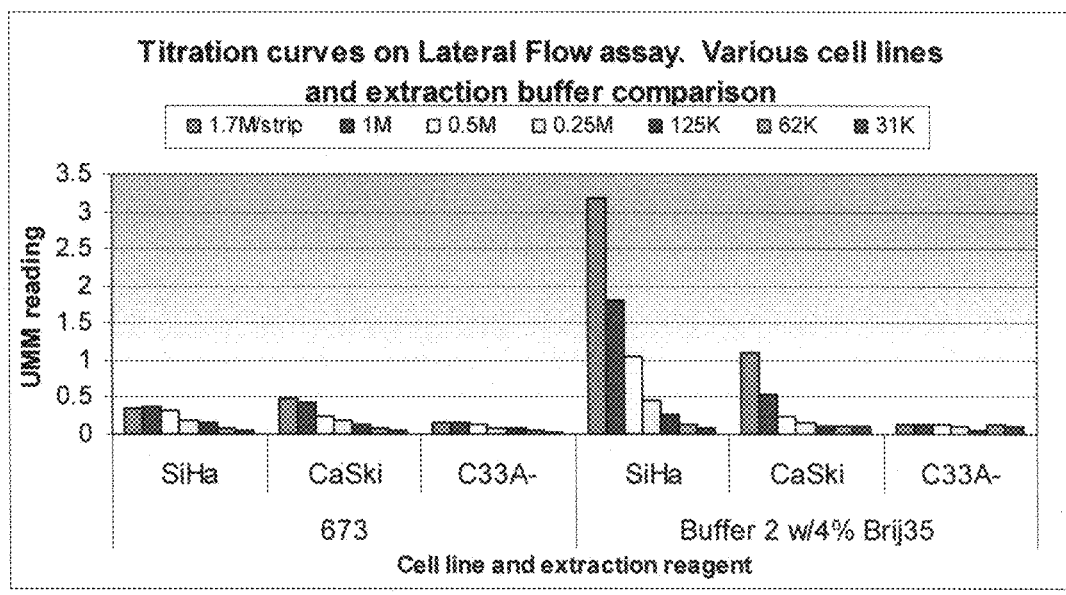
FIG. 3 demonstrates the effect that titrating cell concentration has on the detection of extracted HPV16 E6 protein. Two HPV-positive and one HPV-negative cell lines were used.

In this example, increasing numbers of HPV-16 E6-expressing SiHa and Caski cells were extracted with 4% Brij™35/Buffer 2 described in Examples 2 and 3. The extraction method was similar to that described in Example 3, and a starting concentration of about 9.2 million cells/ml was used. The LF assay differed, however, in that progressively increasing cell numbers were used per LF strip. As indicated in FIG. 3, the cell numbers per strip used in the LF assay were about 31,000; about 62,000; about 125,000; about 250,000; about 500,000; about 1,000,000; or about 1,700,000. Negative controls included extraction of these cells with a neutral pH buffer 673 (described in Example 3) and extraction of HPV-negative C33A cells with either 4% Brij™35/Buffer 2 or buffer 673.

As illustrated in FIG. 3, there was no dose response when the C33A cells were used, and only a limited dose response when neutral pH buffer 673 was used. However, increasing amounts of E6 protein were detected in both HPV-16 E6-expressing cell lines (SiHa and Caski) as a result of using increasing numbers of cells. These results indicated that the assay detected the HPV-16 E6 protein in a dose-response manner.

Example 5

Figure 4:
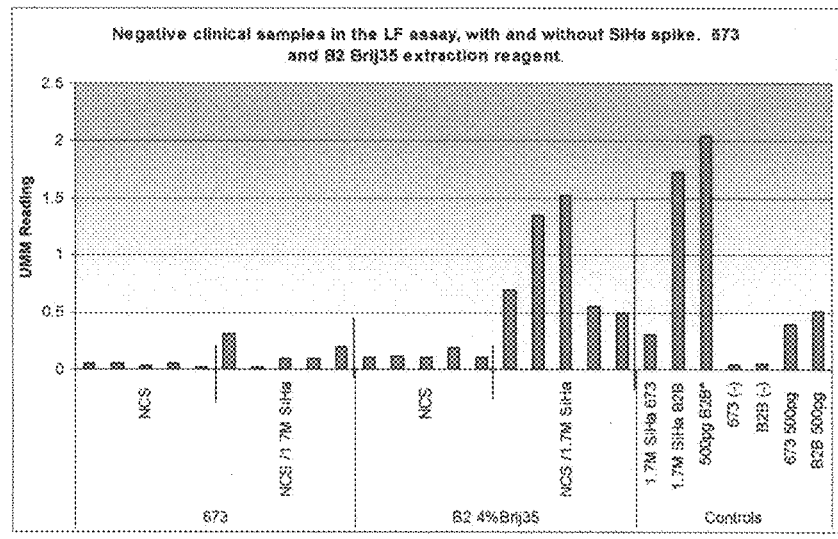
FIG. 4 demonstrates the extraction of HPV16 E6 protein from unfixed negative clinical samples spiked with HPV16-expressing SiHa cells.

Use of 4% Brij™35/Buffer 2 in the Extraction of HPV-16 E6 Protein from Spiked Clinical Samples The example depicted in FIG. 4 illustrates the detection of HPV16 E6 protein in extractions from PAP normal clinical samples that had been combined or "spiked" with HPV16 E6-expressing SiHa cells. The clinical samples used in this example were unfixed, cervical brush samples that tested negative by traditional Pap smear. The samples were first removed from a −80° C. freezer and allowed to thaw at RT for about 10 minutes. Small wire cutters were then used to snip off each brush, which was then placed in a microcentrifuge tube containing a frozen cell pellet of about 10 million SiHa cells. Extraction, neutralization and LF assay of the samples were performed in a manner similar to those described in Examples 3 and 4. For this experiment, either 4% Brij™35/Buffer 2 or neutral buffer 673 (both of which were described in previous examples) was used during the extraction step. The extraction volume for both buffers was approximately 1 ml.

Significant HPV16 E6 protein was detected in the five SiHa-cell-spiked clinical samples extracted using 4% Brij™35/Buffer 2 (FIG. 4). In contrast, extraction of the five non-SiHa spiked samples resulted in a comparatively lower signal. Similarly, use of Buffer 673 to extract either cell type also resulted in a comparatively lower signal. These results suggested that the Brij™35/Buffer 2 could be successfully used in the future to detect the HPV16 E6 protein in clinical samples.

Example 6

Further Optimization of Brij™35/Buffer 2 for Use in Protein Extraction

Figure 5:
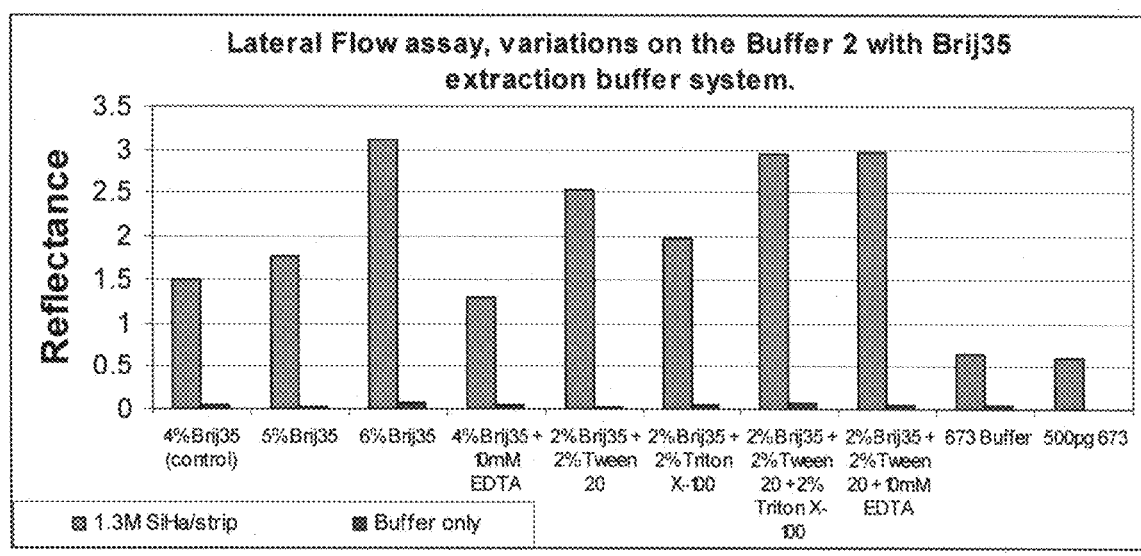
FIG. 5 demonstrates the effect on the detection of extracted HPV16 E6 protein when the Brij™35 concentration in the extraction reagent is increased and when the Brij™35 is combined with other non-ionic detergents such as Triton™X-100 or Tween™-20.

This example illustrates the further optimization of Brij™ 35 extraction using different percentages of Brij™ 35 and/or different combinations of additives. Here, Buffer 2 (described in Example 2) containing varying levels of Brij™ 35 was used to aid in the extraction of the HPV16 E6 from SiHa cells, a cell line transfected with the gene for HPV16 E6 (FIG. 5). In addition, Buffer 2 containing Brij™ 35 in combination with other additives such as EDTA, Tween™-20, or Triton™ X-100 was also tested. For this experiment, the extraction, neutralization and LF assay steps were similar to those described in Examples 2 and 3 except that the level of additive used in the extraction buffer was varied. The amount of additive used in the extraction buffer was either: 4% Brij™35, 5% Brij™ 35, 6% Brij™ 35, 4% Brij™ 35+10 mM EDTA, 2% Brij™ 35+2% Tween-20, 2% Brij™ 35+2% Triton™X-100, 2% Brij™ 35+2% Tween™-20+2% Triton™ X-100, or 2% Brij™ 35+2% Tween™-20+10 mM EDTA. As a control, some samples were extracted with neutral pH buffer 673. The approximate number of cells per LF strip was about 1,300,000.

As is shown in FIG. 5, increasing the percentage of Brij™ 35 from 4% to 6% resulted in enhanced detection of the HPV 16 E6 protein. The assay was also improved by the addition of Triton™ X-100 and/or Twee™n-20 to the Brij™ 35 buffer.

Example 7

Figure 6:
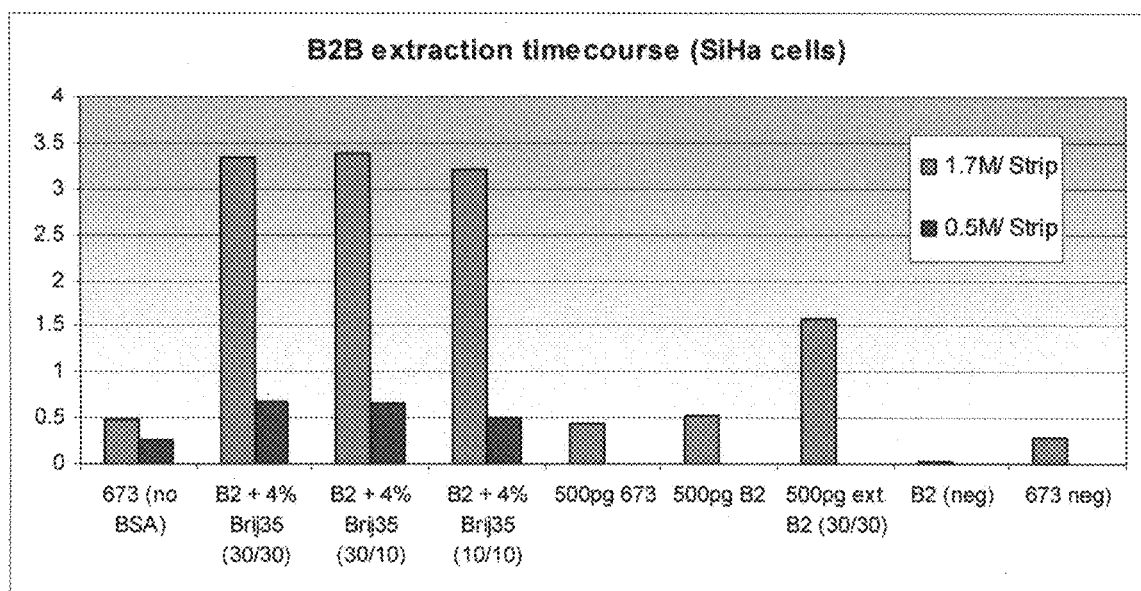
FIG. 6 demonstrates the effect on the detection of extracted HPV16 E6 protein when varying times for extraction and/or neutralization are used.

Effect of Timing of the Extraction and/or Neutralization Steps on the Detection of HPV16 E6 Protein This example illustrates the effect that the timing of the extraction and/or neutralization steps had on the ultimate detection of HPV E6 protein. In this example, the E6 protein was extracted from SiHa cells again generally following the procedures outlined in Example 3. However, in this example, the incubation time for the extraction and/or neutralization steps was changed (FIG. 6). The SiHa cells were extracted at about 10,000,000 cells/ml for either 30 minutes or 10 minutes and neutralized for either 30 minutes or 10 minutes, as indicated in FIG. 6. The stop time for the neutralization step was defined by the time of centrifugation for the clarification step. In addition, for the LF assay, either 1,700,000 or 500,000 SiHa cells were used per strip.

No significant differences in HPV-16 E6 protein were detected when different extraction or neutralization incubation times were used (FIG. 6). This example thus indicates that the assay is not adversely affected when the timing of the extraction and/or neutralization incubation steps is changed from 30 minutes to 10 minutes.

Example 8

Figure 7:
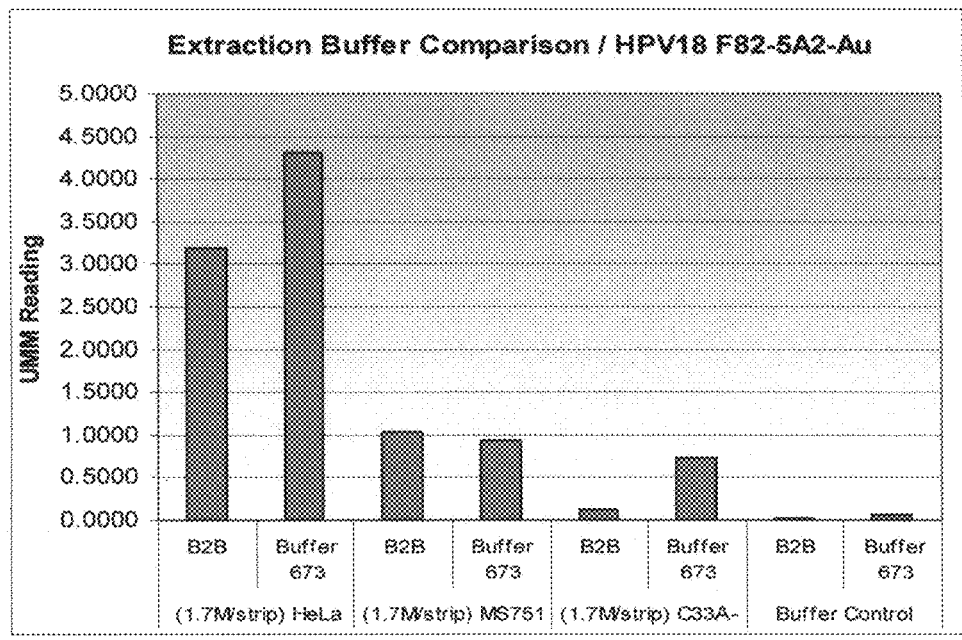
FIG. 7 demonstrates the use of 4% Brij™35/high pH Buffer 2 for extraction of E6 protein derived from HPV strains 18 and 45.

Use of the 4% Brij™35/Buffer 2 to Extract the HPV 18 and HPV 45 Variants of E6 Protein This example illustrates the application of the 4% Brij™35/Buffer 2 extraction system described in Examples 2 and 3 to extract the E6 protein of different strains of HPV (FIG. 7). E6 protein was extracted either from HeLa cells expressing HPV 18 or MS751 cells expressing HPV 45. The HPV negative C33A-cell line was used as a negative control. The extraction and neutralization procedures were similar to those described in Examples 2 and 3. For the LF assay, the equivalent of about 1,700,000 cells of each type was used per LF strip. Also, the colloidal gold used in the LF assay was conjugated with F82-5A2 monoclonal antibody, which recognizes the E6 proteins of HPV strains 18 and 45.

As demonstrated in FIG. 7, the 4% Brij™35/Buffer 2 extraction system can be successfully used to extract HPV18 E6 protein and HPV45 E6 protein.

Example 9

Figure 8:
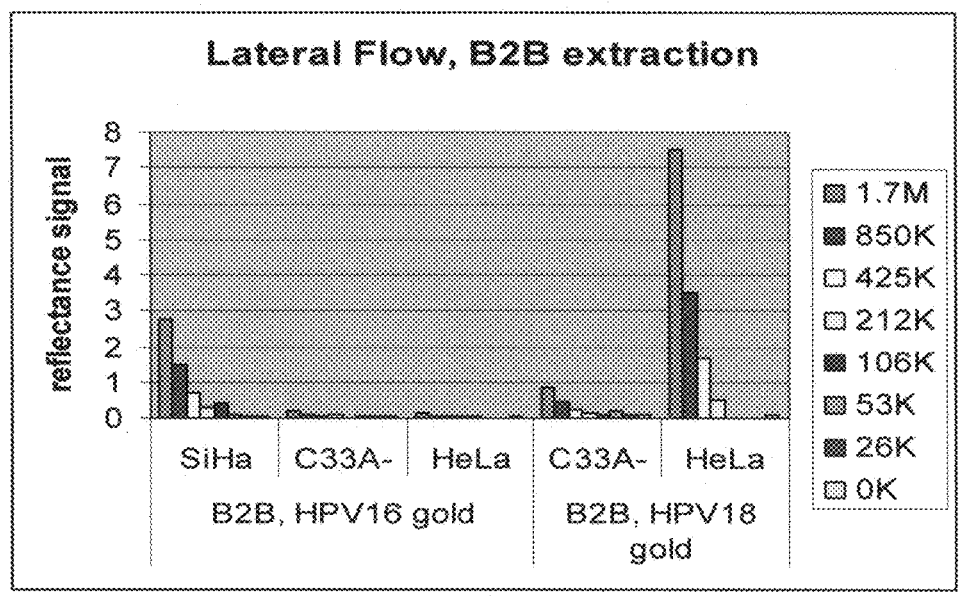
FIG. 8 demonstrates a dose-response effect on the detection of E6 protein derived from HPV strains 16 and 18.

Use of the 4% Brij™35/Buffer 2 to Extract the HPV 16 and HPV 18 Variants of E6 Protein This example compares the 4% Brij™35/Buffer 2 extraction of HPV16 E6 protein with that of HPV 18 E6 protein. The extraction and neutralization steps for the experiment described in FIG. 8 were conducted in a manner similar to those of Example 8. However, this example used SiHa cells expressing HPV16 and HeLa cells expressing HPV 18. As before, C33A-cells were used as a negative control. For the LF assay, increasing numbers of cells (same range as Example 4) were used per LF strip. In addition, anti-HPV16 gold was used in the LF assay of the SiHa cell extracts, while anti-HPV18 gold was used in the LF assay of the HeLa cell extracts.

Figure 9:
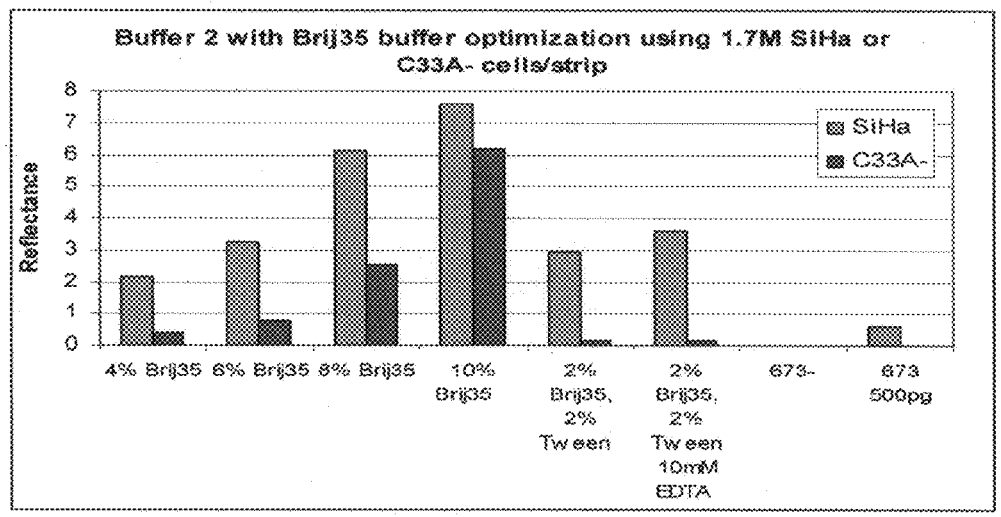
FIG. 9 demonstrates the further optimization of the concentration of Brij™35 (with or without other non-ionic additives) in the extraction reagent.

E6 protein was detected in extracts from the HeLa and SiHa cells (FIG. 9). The detection of both the HPV16 E6 protein and the HPV18 E6 protein occurred in a dose-response manner (FIG. 9).

Example 10

Further Optimization of the Brij™35/Buffer 2 System

This example illustrates the effect of varying the level of Brij™35 from about 4% to about 10% in Buffer 2 (described in Example 2). For the experiment described in FIG. 9, the extraction and neutralization steps were similar to those of Example 3. As in that example, the starting cells were either the HPV16-infected SiHa cells or HPV-negative C33A-cells. Here, however, the percentage of Brij™35 present at the time of extraction was varied. More specifically, the percentages of Brij™35 used were: about 4%, about 6%, about 8% or about 10%. In addition, 2% Brij™35/2% Tween™ 20 and 2% Brij™35/2% Tween™-20/10 mM EDTA were also tested. A LF assay was performed as described herein. About 1.7 million cells were used per LF strip.

As indicated in FIG. 9, the positive signal from the extracts from the SiHa cells increased with increasing Brij™35 concentration. However, the signal also increased in extracts prepared from HPV-negative C33A-cells, resulting in decreased signal-to-noise ratios at higher percentages of Brij™. The signal-to-noise ratio of the assay appeared to be improved, however, when 4% or 6% Brij™ was used. In addition, combining Brij™ with Tween™-20 also appeared to improve the signal-to-noise.

Example 11

Optimization of Extractions from SiHa-Spiked Negative Clinical Samples

Figure 10:
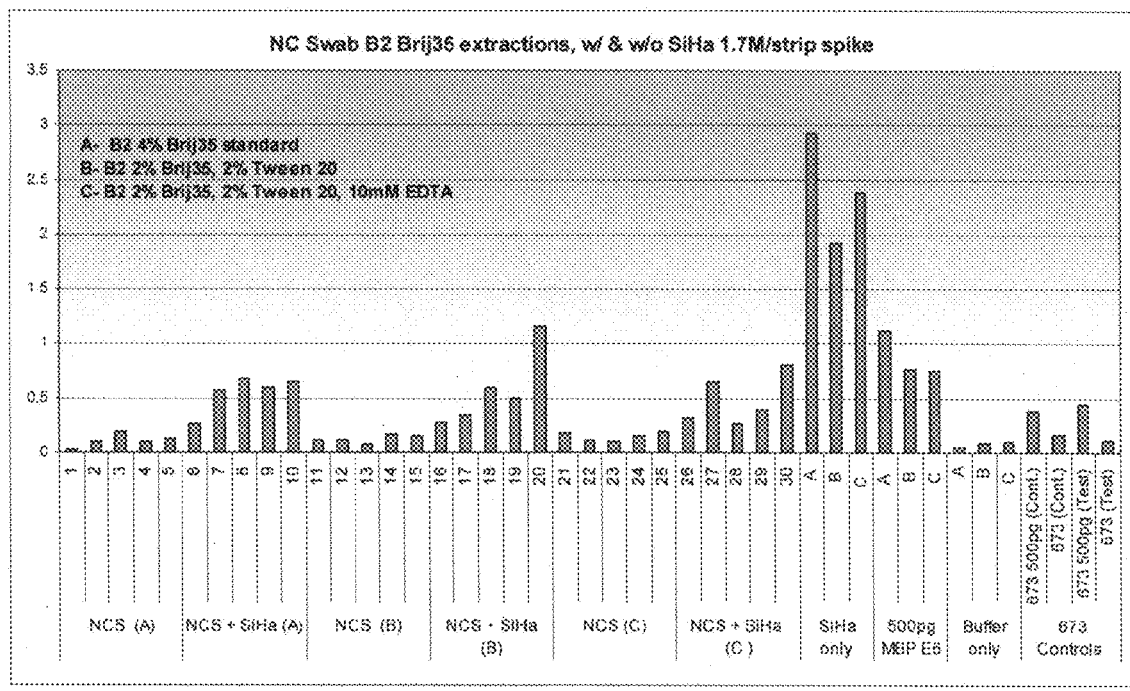
FIG. 10 demonstrates the further optimization of the concentration of Brij™35 (with or without other non-ionic additives) in the extraction reagent and the effect on extraction of HPV16 E6 protein from unfixed negative clinical samples spiked with HPV-expressing cells.

This example illustrates the effect of varying the extraction conditions on the extraction of E6 protein from SiHa-spiked negative clinical samples. Sample preparation as well as the extraction and neutralization steps used here are similar to those used in Example 5. However, in this example the negative clinical samples (NCS) were present on a swab instead of a brush. In addition, the extraction conditions were varied in this experiment to include Buffer 2 with either 4% Brij™35; 2% Brij™35/2% Tween™-20, or; 2% Brij™35/2% Tween™-20/10 mM EDTA (FIG. 10). As indicated, about 1.7 million SiHa cells/strip were used for the LF assay.

As indicated by the results shown in FIG. 10, the 4% Brij™35/Buffer 2 condition may be the superior condition for detecting HPV 16 E6 protein in clinical samples, since the SiHa-spiked samples yielded relatively consistent positive signals, while the negative samples resulted in relatively lower signals (FIG. 10).

Example 12

Figure 11:
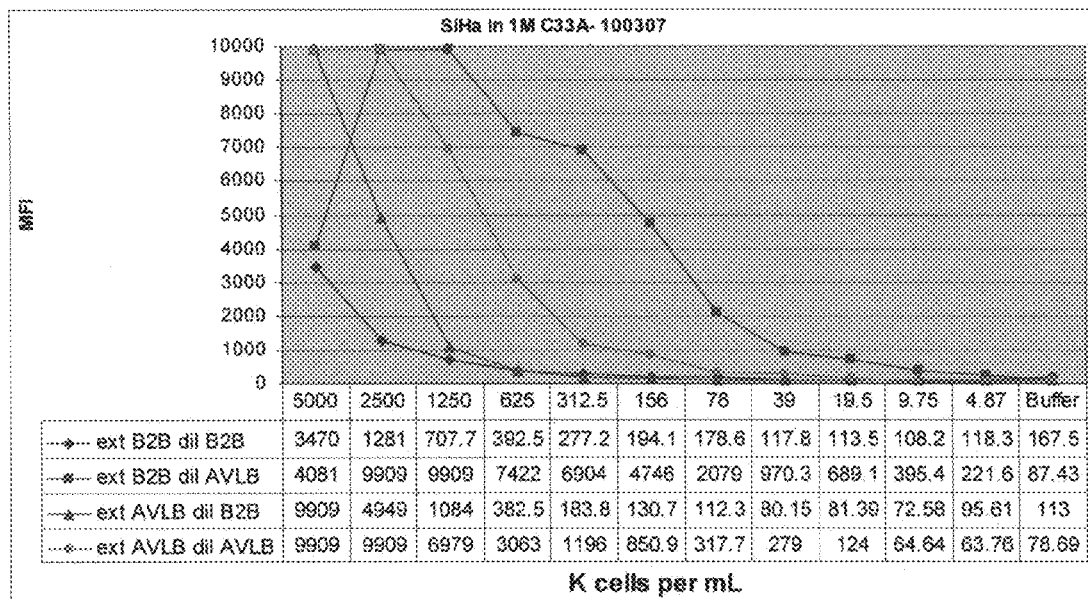
FIG. 11 demonstrates a cytometric bead array (CBA) format to detect HPV16 E6 protein extracted from HPV-expressing SiHa cells.

Extraction of HPV 16 E6 Protein from SiHa Cells in Presence of HPV-Negative Cells This example illustrates the extraction of HPV16 E6 protein from SiHa cells in the presence of HPV-negative C33A-cells. For this example, increasing quantities of SiHa extracts were titrated into buffer containing a fixed quantity (about 1 million/ml) of C33A-cells (FIG. 11). For this experiment, each cell line was extracted separately using either 4% Brij™35/Buffer 2 or Arbor Vita Lysis Buffer (AVLB). AVLB consists of about 50 mM HEPES, pH about pH 7.5, about 1.1% Triton™X-100, about 150 mM NaCl, about 10% glycerol and about 1 mM EGTA. The extraction and neutralization steps were conducted in a manner similar to that of Example 3. However, in this experiment, diluent was prepared consisting of either AVLB or neutralized 4% Brij™35/Buffer 2. C33A-extract was then spiked into each buffer at a level of about 1 million cells/ml. Then, the SiHa cell extracts were serially diluted into the indicated C33A-containing buffers. Samples were analyzed by cytometric bead array (CBA) and read by a fluorimeter.

Results from this experiment revealed that the best condition for detection of E6 protein was 4% Brij™35/Buffer 2 extraction and neutralization followed by dilution in AVLB buffer (FIG. 11). In addition, the level of detection of E6 protein appeared to be about 5000 cells/ml or 500 cells/well (FIG. 11).

Example 13

Extraction of HPV16 E6 Protein from SiHa Cells Fixed in ThinPrep™ or SurePath™ Fixative This example illustrates that the Buffer 2/4% Brij™35 extraction system can be used to extract protein from fixed cells. In the experiment described in FIG. 12, 10 million HPV16 positive SiHa or HPV-negative C33A-cells were added to 1 ml of the indicated fixative or DMEM media for 1 hour at RT. The cells were then spun at 1000 RPM for 15 minutes, pelleted, and resuspended in 1 ml of 4% Brij™35/Buffer 2 described in Example 3. The samples were then subjected to the extraction, neutralization and LF assay steps described in Example 3.

Figure 12:
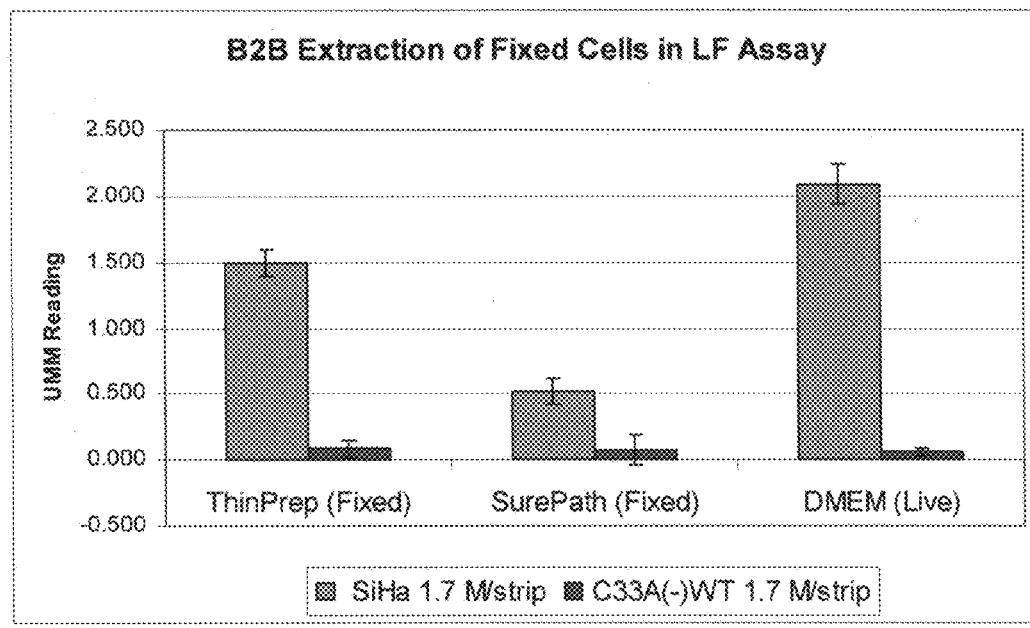
FIG. 12 demonstrates use of 4% Brij™35/high pH Buffer 2 in the extraction of HPV16 E6 protein from either fixed or unfixed cells.

As indicated in FIG. 12, E6 protein present in both Thin-Prep™- and SurePath™-fixed SiHa cells was successfully detected when 4% Brij™35/Buffer 2 was used in the extraction step.

It is evident that from the above results and discussion that the subject methods provide a number of distinct advantages for the molecular analysis of fixed or unfixed cells. In particular, the methods provides a routine method for the production of a protein extract from fixed or unfixed cells in which proteins in the protein extract are detectable in binding assays. Since it is generally difficult to detect certain proteins in fixed or unfixed cells, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for producing a protein extract from fixed or unfixed cells, comprising:
   a) contacting said fixed or unfixed cells with an extraction reagent to produce an intermediate composition having a pH of greater than pH 10.0; and
   b) contacting said intermediate composition with a neutralizing reagent to neutralize said pH of said intermediate composition and produce said protein extract, wherein one or both of said extraction reagent and said neutralizing reagent comprises a polyoxyethylene alkyl ether.

2. The method of claim 1, wherein said extraction reagent comprises a polyoxyethylene alkyl ether, and
   said protein extract of step (b) has a pH of about 6-9.

3. The method of claim 1, wherein said protein extract of step (b) has a pH of about 6-9 and wherein said neutralizing reagent comprises a polyoxyethylene alkyl ether.

4. The method of claim 1, wherein said polyoxyethylene alkyl ether is a polyoxyethylene (n) ether.

5. The method of claim 4, wherein said polyoxyethylene (n) ether is polyoxyethylene (23) lauryl ether.

6. The method of claim 5, wherein the concentration of said polyoxyethylene (23) lauryl ether in said extraction reagent is within about 2-6% (v/v).

7. The method of claim 6, wherein said extraction reagent further comprises about 0.1N NaOH, about 50 mM TriSodium Citrate, and has a pH of about 12.5 to 12.9.

8. The method of claim 7, wherein said extraction reagent further comprises an octylphenolpoly(ethyleneglycolether)$_x$ detergent or a polysorbate detergent, or mixture thereof.

9. The method of claim 7, wherein said extraction reagent further comprises octylphenol ethylene oxide detergent or polysorbate 20 detergent, or mixture thereof.

10. The method of claim 9, wherein the concentration of said octylphenol ethylene oxide or polysorbate 20 detergent or both is within about 2-6% (v/v).

11. The method of claim 1, wherein said neutralizing reagent is a Tris-based buffer.

12. The method of claim 1, wherein said contacting said fixed or unfixed cells with said extraction reagent in step (a) occurs for between 10 and 30 minutes.

13. The method of claim 1, wherein said contacting said intermediate composition with a neutralizing reagent to neutralize said pH of said intermediate composition occurs for between 10 and 30 minutes.

14. The method of claim 4, wherein said polyoxyethylene (n) ether is one or more of polyoxyethylene (23) lauryl ether, $(CH_3(CH_2)_{10}CH_2(OCH_2CH_2)_nOH$, n~23): polyoxyethylene (4) lauryl ether $(CH_3(CH_2)_{10}CH_2(OCH_2CH_2)_nOH$, n~4); polyoxyethylene (2) cetyl ether $(C_{16}H_{33}(OCH_2CH_2)nOH$, n~2); polyoxyethylene (10) cetyl ether $(C_{16}H_{33}(OCH_2CH_2)_nOH$, n~10); polyoxyethylene (20) cetyl ether $(C_{16}H_{33}(OCH_2CH_2)_nOH$, n~20); polyoxyethylene (2) stearyl ether, $(C_{18}H_{37}(OCH_2CH_2)_nOH$, n~2); polyoxyethylene (10) stearyl ether $(C_{18}H_{37}(OCH_2CH_2)_nOH$, n~10); polyoxyethylene (20) stearyl ether $(C_{18}H_{37}(OCH_2CH_2)_nOH$, n~20); polyoxyethylene (2) oleyl ether $(C_{18}H_{35}(OCH_2CH_2)_nOH$, n~2); polyoxyethylene (2) oleyl ether; $(C_{18}H_{35}(OCH_2CH_2)_nOH$, n~2); polyoxyethylene (10) oleyl ether $(C_{18}H_{35}(OCH_2CH_2)_nOH$, n~10); polyoxyethylene (20) oleyl ether $(C_{18}H_{35}(OCH_2CH_2)_nOH$, n~20); polyoxyethylene (100) stearyl ether, $(C_{18}H_{37}(OCH_2CH_2)_{21}OH$, n~100); or polyoxyethylene (21) stearyl ether $(C_{18}H_{37}(OCH_2CH_2)_nOH$, n~21).

15. The method of claim 1, further comprising: obtaining a cellular sample comprising said fixed or unfixed cells prior to step a), wherein said cellular sample contains or is suspected of containing a target protein.

16. The method of claim 15, wherein said fixed or unfixed cells are fixed cervical cells, and said target protein is a human Papillomavirus (HPV) E6 protein.

17. The method of claim 16, wherein said fixed cervical cells are present in an ethanol-based or methanol-based transport medium.

18. The method of claim 15, wherein said cellular sample is obtained from an individual.

19. The method of claim 1, wherein said intermediate composition having a pH of greater than pH 10.0 has a pH that is in the range of about pH 11.0 to about pH 13.

20. The method of claim 1, wherein said extraction reagent does not comprise a denaturant.

21. The method of claim 1, wherein said fixed or unfixed cells are from a cell sample in which a target viral protein is present or suspected of being present.

22. The method of claim 21, wherein said polyoxyethylene alkyl ether is polyoxyethylene (n) ether.

23. The method of claim 22, wherein said polyoxyethylene (n) ether is polyoxyethylene (23) lauryl ether which is comprised by the extraction reagent at a concentration of about 2-6% (v/v).

24. The method of claim 23, wherein said extraction reagent further comprises about 0.1N NaOH, about 50 mM TriSodium Citrate, and a pH of about 12.5 to 12.9.

25. The method of claim 24, wherein said extraction reagent further comprises an octylphenolpoly(ethyleneglycolether)$_x$ detergent or a polysorbate detergent, or mixture thereof.

26. The method of claim 25, wherein said extraction reagent further comprises octylphenol ethylene oxide detergent or polysorbate 20 detergent, or a mixture thereof.

27. The method of claim 26, wherein the concentration of said octylphenol ethylene oxide detergent or polysorbate 20 detergent, or both is within about 2-6% (v/v).

28. The method of claim 21, wherein said neutralizing reagent is a Tris-based buffer.

29. The method of claim 21, wherein said contacting said intermediate composition with said neutralizing reagent to neutralize said pH of said intermediate composition occurs for between 10 and 30 minutes.

30. The method of claim 21, wherein said contacting said intermediate composition with a neutralizing reagent to neutralize said pH of said intermediate composition occurs for between 10 and 30 minutes.

31. The method of claim 22, wherein said polyoxyethylene (n) ether is one or more of: polyoxyethylene (23) lauryl ether, $(CH_3(CH_2)_{10}CH_2(OCH_2CH_2)_nOH$, n~23): polyoxyethylene (4) lauryl ether $(CH_3(CH_2)_{10}CH_2(OCH_2CH_2)_nOH$, n~4); polyoxyethylene (2) cetyl ether $(C_{16}H_{33}(OCH_2CH_2)_nOH$, n~2); polyoxyethylene (10) cetyl ether $(C_{16}H_{33}(OCH_2CH_2)_nOH$, n~10); polyoxyethylene (20) cetyl ether $(C_{16}H_{33}(OCH_2CH_2)_nOH$, n~20); polyoxyethylene (2) stearyl ether, $(C_{18}H_{37}(OCH_2CH_2)_nOH$, n~2); polyoxyethylene (10) stearyl ether $(C_{18}H_{37}(OCH_2CH_2)_nOH$, n~10); polyoxyethylene (20) stearyl ether $(C_{18}H_{37}(OCH_2CH_2)_nOH$, n~20); polyoxyethylene (2) oleyl ether $(C_{18}H_{35}(OCH_2CH_2)_nOH$, n~2); polyoxyethylene (2) oleyl ether; $(C_{18}H_{35}(OCH_2CH_2)_nOH$, n~2); polyoxyethylene (10) oleyl ether $(C_{18}H_{35}(OCH_2CH_2)_nOH$, n~10); polyoxyethylene (20) oleyl ether $(C_{18}H_{35}(OCH_2CH_2)_nOH$, n~20); polyoxyethylene (100) stearyl ether, $(C_{18}H_{37}(OCH_2CH_2)_{21}OH$, n~100); or polyoxyethylene (21) stearyl ether $(C_{18}H_{37}(OCH_2CH_2)_nOH$, n~21).

32. The method of claim 21, wherein said cells in said cell sample are fixed with a chemical fixative.

33. The method of claim 32, wherein said chemical fixative is selected from the group consisting of alcohols, aldehydes, ketones, osmium tetroxide, acetic acid, picric acid, heavy metal ion salts, and propylene glycol.

34. The method of claim 33, wherein said alcohol is methanol or ethanol; said aldehyde is gluteraldehyde or formaldehyde; and said ketone is acetone.

35. The method of claim 32, wherein said fixed cells are present in an ethanol-based or methanol-based transport medium.

36. The method of claim 21, further comprising: receiving the cell sample prior to step a).

37. The method of claim 21, wherein said target viral protein is encoded by a pathogenic virus.

38. The method of claim 37, wherein said pathogenic virus is selected from the group consisting of HIV, Ebola virus, Marburg virus, hepatitis virus, respiratory syncytial virus (RSV), herpes simplex virus (HSV), and human papilloma virus (HPV).

39. The method of claim 21, wherein said target viral protein is E6 or E7 protein of HPV.

40. The method of claim 39, wherein said HPV is HPV strain 4, 11, 20, 24, 28, 36, 48, 50, 16, 18, 31, 35, 30, 39, 45, 51, 52, 56, 59, 58, 33, 66, 68, 69, 26, 53, 73, or 82.

41. The method of claim 39, wherein said HPV is an oncogenic HPV strain selected from the group consisting of HPV 26, HPV 53, HPV 66, HPV 73, HPV 82, HPV 16, HPV 18, HPV 31, HPV 35, HPV 30, HPV 39, HPV 45, HPV 51, HPV 52, HPV 56, HPV 59, HPV 58, HPV 33, HPV 66, HPV 68, HPV 69, and HPV 82.

42. The method of claim 1, wherein said fixed or unfixed cells are fixed cells.

43. The method of claim 1, wherein said fixed or unfixed cells are unfixed cells.

44. The method of claim 1, wherein said fixed or unfixed cells are mammalian cells.

45. The method of claim 1, wherein said fixed or unfixed cells are human cells.

* * * * *